(12) United States Patent
Muraishi et al.

(10) Patent No.: US 7,858,041 B2
(45) Date of Patent: Dec. 28, 2010

(54) FLUID DISPENSER FOR FLUID IN ASSAY

(75) Inventors: Katsuaki Muraishi, Kanagawa (JP); Tatsuo Fujikura, Saitama (JP); Shinya Takai, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 974 days.

(21) Appl. No.: 11/514,885

(22) Filed: Sep. 5, 2006

(65) Prior Publication Data

US 2007/0053797 A1    Mar. 8, 2007

(30) Foreign Application Priority Data

Sep. 2, 2005    (JP)    ............................. 2005-255012

(51) Int. Cl.
*B01L 3/02* (2006.01)
(52) U.S. Cl. ........................... 422/100; 422/63; 422/67; 422/68.1
(58) Field of Classification Search ................. 422/100, 422/63–68.1
See application file for complete search history.

(56) References Cited

U.S. PATENT DOCUMENTS

| | | | | |
|---|---|---|---|---|
| 4,586,546 A * | 5/1986 | Mezei et al. | .................... | 141/2 |
| 5,055,263 A | 10/1991 | Meltzer | | |
| 5,306,510 A * | 4/1994 | Meltzer | ........................ | 422/65 |
| 5,497,670 A * | 3/1996 | Carl | ......................... | 73/863.32 |
| 6,006,800 A * | 12/1999 | Nakano | ....................... | 141/130 |
| 6,008,893 A | 12/1999 | Roos et al. | | |
| 6,143,252 A | 11/2000 | Haxo, Jr. et al. | | |
| 6,325,114 B1 * | 12/2001 | Bevirt et al. | ................. | 141/130 |
| 6,506,611 B2 * | 1/2003 | Bienert et al. | ............... | 436/180 |
| 6,558,623 B1 * | 5/2003 | Ganz et al. | .................... | 422/63 |
| 7,314,598 B2 * | 1/2008 | Nishino | ...................... | 422/100 |
| 2002/0051737 A1 * | 5/2002 | Sollbohmer et al. | ......... | 422/100 |
| 2003/0124735 A1 | 7/2003 | Nanthakumar et al. | | |
| 2004/0234420 A1 * | 11/2004 | Yiu | ............................ | 422/100 |
| 2006/0034732 A1 * | 2/2006 | Bargh et al. | ................. | 422/100 |
| 2006/0133965 A1 * | 6/2006 | Tajima et al. | ............... | 422/100 |

FOREIGN PATENT DOCUMENTS

| | | |
|---|---|---|
| DE | 198 35 833 A1 | 2/2000 |
| JP | 6-167443 A | 6/1994 |
| WO | WO 2004/059301 A1 | 7/2004 |

* cited by examiner

*Primary Examiner*—Brian R Gordon
(74) *Attorney, Agent, or Firm*—Sughrue Mion, PLLC

(57) ABSTRACT

A fluid dispenser for surface plasmon resonance (SPR) assay apparatus includes a first pipette device on a first pipette head, and a second pipette device on a second pipette head. In a standby state, the first pipette head is set in an upper position, a coil spring and a stopper set the second pipette head together with the first pipette head, and locate the second pipette head in a high position. While the first and second pipette devices are in an aspirating position, a driving mechanism sets the first pipette head in a lower position. A blocking mechanism sets the second pipette head in a high position against the coil spring. First, third and fifth pipette tips is positioned lower than second, fourth and sixth pipette tips, to access a well. The first to sixth pipette tips, while in an assay position, are equally lowered.

10 Claims, 13 Drawing Sheets

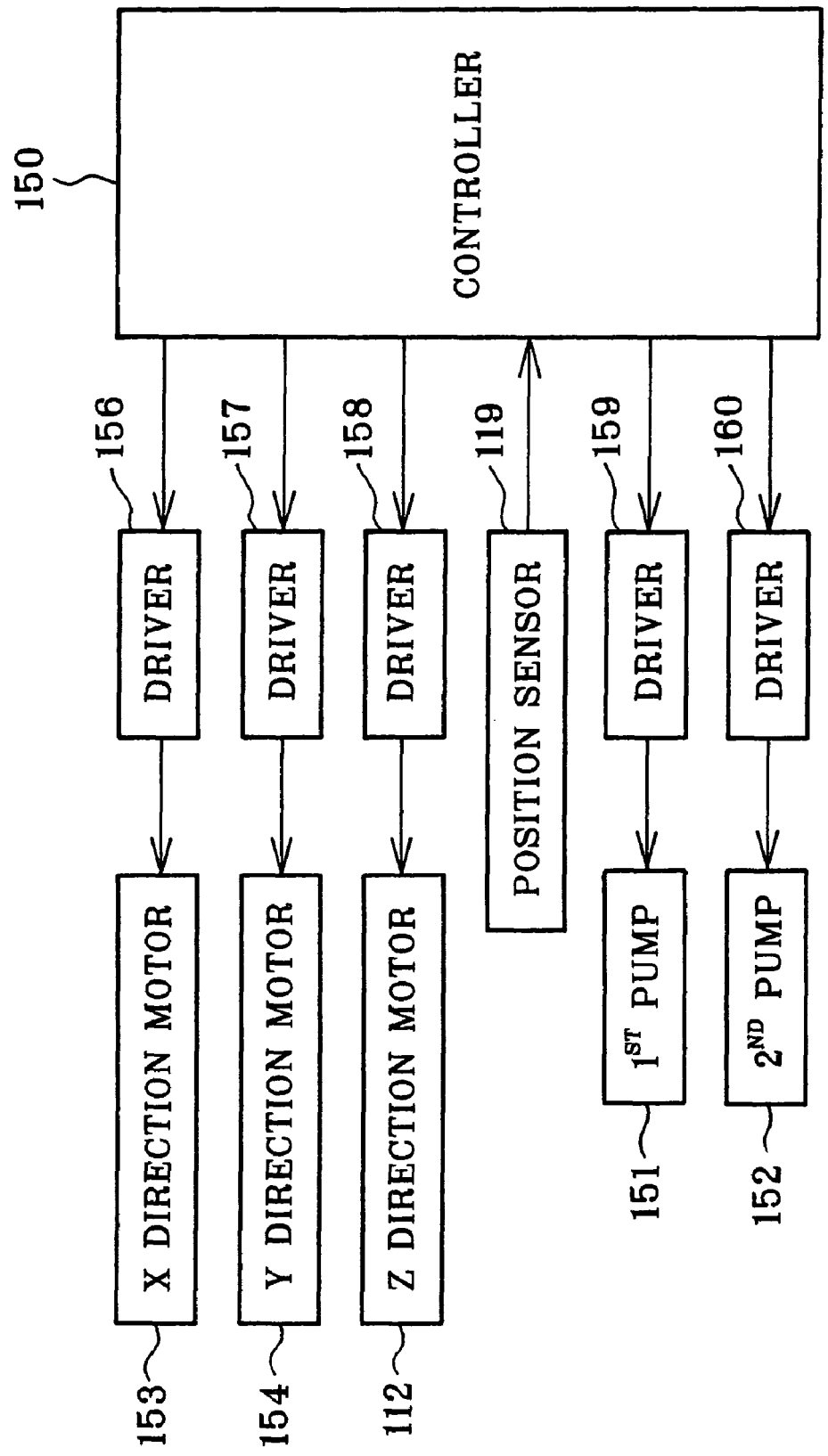

FLUID DISPENSER FOR FLUID IN ASSAY

BACKGROUND OF THE INVENTION

1. Field of the Invention

The present invention relates to a fluid dispenser for fluid in assay. More particularly, the present invention relates to a fluid dispenser for fluid in assay, in which pipette devices can be moved up and down selectively even with a simple structure of a pipette head.

2. Description Related to the Prior Art

An assay apparatus for assay in utilizing attenuated total reflection is used for various kinds of studies in a biochemical field or the like, for example to study interaction of protein, DNA and various biomaterials, and to select candidate drugs by screening. Also, the technique is useful in the fields of the clinical medicine, food industries and the like.

A surface plasmon resonance (SPR) sensor is known as an assay apparatus for assay in utilizing attenuated total reflection. A thin film/dielectric interface of a metal film is fitted on a dielectric block. Light is directed to the thin film/dielectric interface in a manner conditioned for total reflection. Surface plasmon is a term to mean the compressional wave created on the surface of the metal and included in plasmon as quantized expression of the compressional wave. Free electrons in a metal vibrate to generate the compressional wave.

In the assay apparatus, the sensing surface is positioned opposite to the interface where the metal thin film is connected with the dielectric block. The sensing surface is caused to create surface plasmon resonance. Reaction of samples is assayed by detecting the SPR on the sensing surface.

Illuminating light is applied to an interface between the thin film and the prism or a surface back to the sensing surface at an angle of incidence equal to or more than a critical angle to satisfy a condition of total reflection. Then total reflection of the illuminating light occurs. Upon the total reflection created on the metal/dielectric interface, a small component of the light passes through the metal film without reflection, and penetrates to the sensing surface. A wave of the penetrating component is called an evanescent wave. Surface plasmon resonance (SPR) is created when frequency of the evanescent wave coincides with that of the surface plasmon. In response to this, intensity of the reflected light attenuates remarkably. In the assay apparatus, the attenuation in the reflected light reflected by the metal/dielectric interface is detected, to recognize creation of the SPR on the sensing surface.

A resonance angle or an angle of incidence of light for creation of surface plasmon resonance depends upon a refractive index of a medium of transmission of evanescent waves and surface plasmon. In other words, a change in the refractive index of the medium of transmission causes a change in the resonance angle of creation of SPR. The substance or sample in contact with the sensing surface is the medium for transmitting the evanescent waves and surface plasmon. When binding, dissociation or other reaction occurs on the sensing surface between two molecules or samples, the resonance angle changes because of a change in the refractive index of the medium of transmission. The SPR assay apparatus finds the changes in the resonance angle, to assay the interaction between the molecules or samples.

An assay apparatus for assay in utilizing attenuated total reflection is used for various kinds of studies in a biochemical field or the like, for example to study interaction of protein, DNA and various biomaterials, and to select candidate drugs by screening. Also, the technique is useful in the fields of the clinical medicine, food industries and the like. A sample or biomaterial, such as protein, is handled as sample fluid.

JP-A 6-167443 discloses an SPR assay apparatus in which an optical system of Kretschmann configuration is used for incidence of light to the metal film. According to the Kretschmann configuration, the thin film/dielectric interface of the metal film is fitted on a prism, which condenses light and directs the light to the thin film/dielectric interface in a manner conditioned for total reflection. A sensing surface is overlaid inside the flow channel, for immobilizing the sample. A flow channel is disposed so that the sensing surface lies therein. Ligand fluid is introduced to the flow channel for immobilizing the ligand on the sensing surface. After this, analyte fluid is introduced for contact of the analyte and the ligand, to assay the interaction between those.

For assay, at first liquid buffer is introduced to a flow channel and flows on to a sensing surface. Then measurement of an output signal is started. After this, analyte fluid is introduced. The liquid buffer in the flow channel is caused by the analyte fluid to flow out and exit from an orifice of the flow channel. The analyte fluid is kept stored in the flow channel, before the liquid buffer is introduced to terminate the measurement of the signal. It is possible to detect a baseline of the signal and detect a signal in the period including step of interaction between analyte and ligand, and their dissociation.

To introduce the analyte fluid to the sensing surface, a fluid dispenser including a pipette device is used. The pipette device is useful because of easy loading and unloading to an orifice of the flow channel in view of rapid assay for a great number of sensor units in a large scale.

The flow channel has a U shape as viewed in a section, and two end orifices open in an upper surface. The fluid dispenser has two of the pipette devices disposed at a pitch of the orifices of the flow channel. A first one of the pipette devices is to aspirate the analyte fluid from a multi well plate as reservoir, and then to dispense the acquired analyte fluid into the flow channel. A second one of the pipette devices is to aspirate the liquid buffer previously filled in the flow channel. For the fluid dispenser to introduce fluid into the flow channel, pipette tips of the pipette devices are inserted in the end orifices of the flow channel. The first pipette device dispenses the analyte fluid at the same time as the second pipette device draws the liquid buffer.

A known example of the fluid dispenser includes a pipette head with a pair of the pipette devices, and a shifter for shifting the pipette head. As an example of shifter, a robot device of a perpendicular coordinate type, a multi joint type and the like can be used. It is possible for the pipette head to access an aspirating position and assay position with high precision, the aspirating position being used for drawing the analyte fluid from the multi well plate by aspiration.

To draw the analyte fluid from the multi well plate by the pipette head, only the first one of the pipette devices is inserted in the multi well plate. The second does not require using at the multi well plate. If both of the pipette devices are moved down, the second is likely to interfere with unwanted objects. Thus, the multi well plate of a normally used type cannot be used in combination. There has been an idea of use of a shifter, associated with the pipette head, for moving each pair of the pipette devices up and down If a shifter for moving up and down each pair of the pipette devices is associated with the pipette head, the pipette head has an excessively complicated structure, and has a great size. Also, a motor must be used for each of the shifters, and will raise the manufacturing cost. Furthermore, the weight of the pipette head will be very heavy, to lower efficiency in operation due to reduction of the speed of moving the pipette head.

SUMMARY OF THE INVENTION

In view of the foregoing problems, an object of the present invention is to provide a fluid dispenser for fluid in assay, in which pipette devices can be moved up and down selectively even with a simple structure of a pipette head.

In order to achieve the above and other objects and advantages of this invention, a fluid dispenser is provided, having a dispensing head, movable between an aspirating position and an assay position, for, when in the aspirating position, aspirating sample by accessing one of wells in a multi well plate in a downward accessing direction, and for, when in the assay position, introducing the sample by accessing in a downward accessing direction into a flow channel in a sensor unit of which a sensing surface is adapted to assay reaction of the sample flowing through the flow channel, the dispensing head including at least one couple of pipette devices including first and second pipette devices, the first pipette device being set in the well to aspirate the sample, and then set in a first orifice of the flow channel to dispense the sample, the second pipette device being set in a second orifice of the flow channel to aspirate fluid in synchronism with dispensation of the first pipette device. The fluid dispenser includes first and second heads for supporting the first and second pipette device in an independent manner from one another. A driving mechanism shifts up or down the first head when the dispensing head is in the aspirating position or the assay position, to cause the first head to move between a first position and a second position, the first head, when in the first position, being positioned low to set a pipette tip of the first pipette device in the well or the first orifice, and when in the second position, being positioned higher than the first position to set the pipette tip away from the well or the first orifice. A guide mechanism supports the second head movably in a vertical shifting direction of the first head and relatively thereto. There is a stopper portion of the first head, for engagement with second head when a pipette tip of the second pipette device is positioned as high as the pipette tip of the first pipette device, to prevent the second head from moving further downwards. A biasing mechanism biases the second head toward the stopper portion.

While the first and second pipette devices are in the assay position, the driving mechanism sets the first pipette head in the lower position, and the biasing mechanism and the stopper set the second pipette head together with the first pipette head, and locate the second pipette head in a low position.

Furthermore, a blocking mechanism is disposed in the aspirating position, for preventing the second pipette head from moving down.

In a standby state, the first pipette head is set in the upper position, the biasing mechanism and the stopper set the second pipette head together with the first pipette head, and locate the second pipette head in a high position. While the first and second pipette devices are in the aspirating position, the driving mechanism sets the first pipette head in the lower position. The blocking mechanism sets the second pipette head in the high position against the biasing mechanism, so that a height of the first pipette tip is lower than a height of the second pipette tip, to access the well.

Furthermore, a moving unit is provided with the support mechanism secured thereto, for moving the first and second pipette heads together in a horizontal direction crosswise to a direction of moving up and down, for setting the first and second pipette devices in the aspirating position and the assay position.

The first pipette head includes first to Nth pipette nozzles. The first pipette device includes N pipette tips, secured to respectively an end of the first to Nth pipette nozzles, for constituting the first pipette tip. The second pipette head includes (N+1)th to (2N)th pipette nozzles, arranged alternately with the first to Nth pipette nozzles, for constituting one pipette nozzle array. The second pipette device includes N pipette tips, secured to respectively an end of the (N+1)th to (2N)th pipette nozzles, for constituting the second pipette tip.

The driving mechanism includes a nut portion secured to the first pipette head. A threaded rod is inserted in the nut portion, and coupled helically therewith. A motor rotates the threaded rod, to shift the first pipette head with the nut portion.

The blocking mechanism includes a projecting rod disposed to project from the second pipette head. A second stopper is disposed in a path of the projecting rod, for engagement therewith, to stop the second pipette head from moving down.

The support mechanism includes a slide rail portion. Furthermore, a slidable projection is disposed to project from the first pipette head, for engagement with the slide rail portion in a slidable manner.

The guide mechanism includes a slide rail portion disposed to extend on the first pipette head. A slidable projection is disposed to project from the second pipette head, for engagement with the slide rail portion in a slidable manner.

Furthermore, a detection projection is disposed to project from one of the first pipette head and the support mechanism. A position sensor is secured to a remaining one of the first pipette head and the support mechanism, for detecting setting of the first pipette head in the upper position.

Also, a fluid dispenser is provided, and includes a first pipette device, having a first pipette tip, for insertion in a well for storing sample when set in an aspirating position, and for aspirating the sample from the well. The first pipette device, when set in an assay position after fluid aspiration, is inserted in a first orifice included in first and second orifices disposed in a sensor unit, and then dispenses the sample into the first orifice, for flow of the sample to a sensing surface in a flow channel disposed to extend between the first and second orifices. A second pipette device has a second pipette tip, for insertion in the second orifice upon setting in the assay position, and for aspirating sample having been introduced in the flow channel. The fluid dispenser includes first and second pipette heads for supporting respectively the first and second pipette devices. A support mechanism supports the first pipette head in a manner movable up and down. A driving mechanism shifts the first pipette device between lower and upper positions. A guide mechanism is disposed on the first pipette head, for guiding the second pipette head in a manner movable up and down. A stopper is secured to the first pipette head, for engagement with one contact portion of the second pipette head when the first and second pipette tips are at heights equal to each other, for stopping the second pipette head from moving down. A biasing mechanism biases the second pipette head in a direction for contact of the contact portion with the stopper.

Consequently, pipette devices in the fluid dispenser for fluid in assay can be moved up and down selectively even with a simple structure of a pipette head.

BRIEF DESCRIPTION OF THE DRAWINGS

The above objects and advantages of the present invention will become more apparent from the following detailed description when read in connection with the accompanying drawings, in which:

FIG. 11 is a block diagram illustrating circuit arrangement of a fluid dispenser;

DETAILED DESCRIPTION OF THE PREFERRED EMBODIMENT(S) OF THE PRESENT INVENTION

Figure 1A:
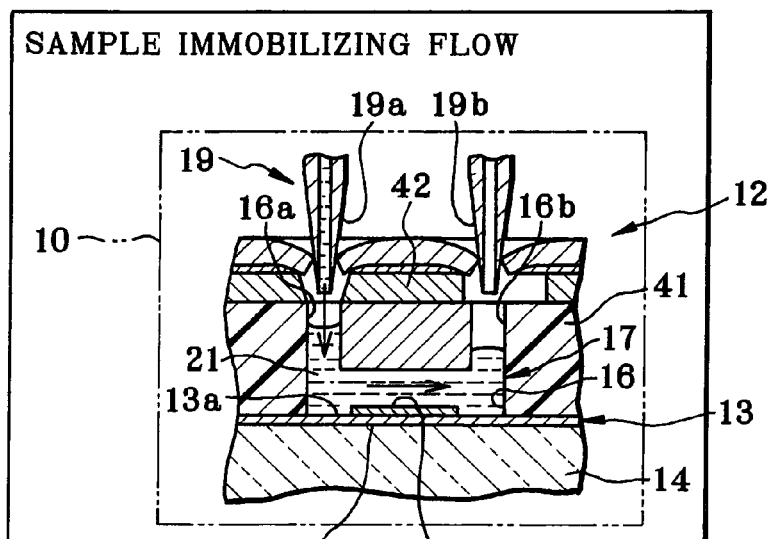
FIG. 1A is an explanatory view in section illustrating a step of a sample immobilizing flow in an assay system.
Figure 1B:
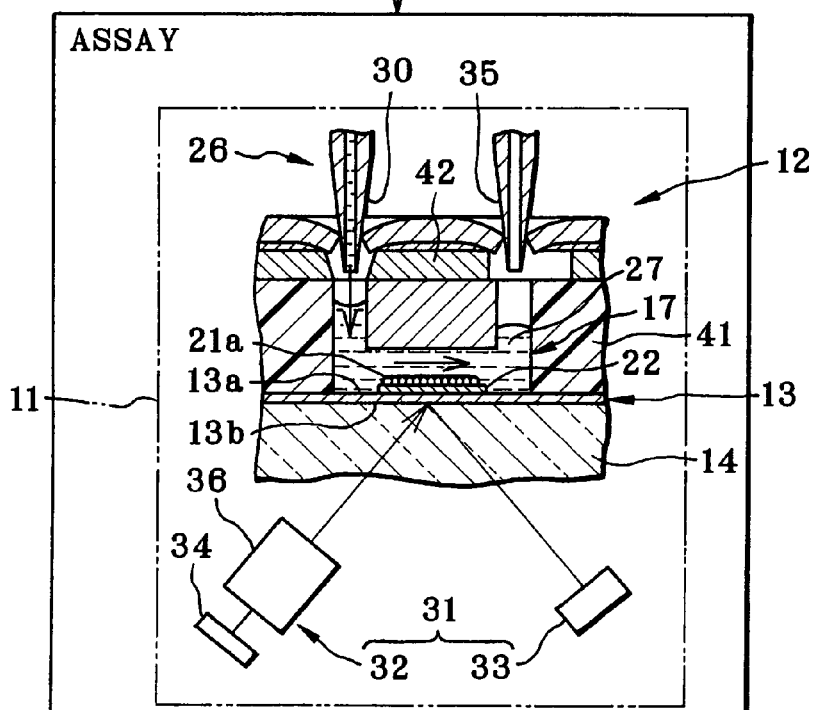
FIG. 1B is an explanatory view in section illustrating steps of assay and data analysis in the assay apparatus.

In FIGS. 1A and 1B, a process of surface plasmon resonance (SPR) assay includes steps of immobilization, assay and data analysis. To this end, an assay system includes sample immobilizing equipment 10, an assay apparatus 11 and a data analyzer 91 of FIG. 4.

A sensor unit 12 for SPR assay issued for assay. The sensor unit 12 includes a thin film of metal 13, a prism 14, and a flow channel 16. A sensing surface 13a is a first surface of the thin film 13 to generate surface plasmon resonance. A second surface of the thin film 13 is an interface 13b where the prism 14 is overlaid with the thin film 13, the interface 13b reflecting light by total reflection. The flow channel 16 is opposed to the sensing surface 13a, and is supplied with ligand, analyte or other fluid for flow.

An example of material for the thin film 13 is gold (Au) or the like. A thickness of the thin film 13 is 50 nm. The thickness can be changed for the suitability in view of the material of the thin film 13, a wavelength of light to be applied, and the like. The prism 14 is a transparent dielectric block, and overlaid with the thin film 13. Illuminating light is condensed by the prism 14 for application to the interface 13b to satisfy the total reflection condition. The flow channels 16 are in the U shape. Ends of the flow channels 16 respectively include a first orifice 16a and a second orifice 16b. The first orifice 16a as entrance receives introduction of a sample fluid. The second orifice 16b as exit is accessed for draining the sample fluid. A horizontal width or diameter of the flow channels 16 is approximately 1 mm. An interval between the first and second orifices 16a and 16b of the flow channel 16 is approximately 10 mm.

A lower side of the flow channels 16 where the flow cell recess is open is enclosed by the prism 14 having the sensing surface 13a. There are defined sensor cells or measuring cells 17 each of which is a portion of the sensing surface 13a closed by the portion about the flow cell recess. In the present embodiment, the sensor unit 12 has plural sensor cells 17, for example three. See FIG. 2.

A sample immobilizing flow is for binding of ligand on the sensing surface 13a. At first, the sensor unit 12 is set in the sample immobilizing equipment 10. A dual pipette assembly 19 is included in the sample immobilizing equipment 10, and has a first pipette device 19a and a second pipette device 19b. The first pipette device 19a is set at the first orifice 16a. The second pipette device 19b is set at the second orifice 16b. The first pipette device 19a introduces fluid to the flow channel 16. The second pipette device 19b aspirates and draws fluid from the flow channel 16. The introduction with the first pipette device 19a is at the same time as drawing with the second pipette device 19b. Ligand fluid 21 as sample fluid, as a fluid which contains ligand or biomaterial and fluid medium, is introduced through the first orifice 16a by the dual pipette assembly 19.

An immobilizing linker film 22 is overlaid on the thin film 13 at the center of the sensing surface 13a. The linker film 22 is previously produced in the course of manufacturing the sensor unit 12. As the linker film 22 is a basis for immobilizing the ligand, various materials are available for selective use according to the type of the ligand to be immobilized.

In the sample immobilizing equipment 10, pre-treatment before a ligand immobilizing flow with the ligand fluid 21 is wetting of the linker film 22 by use of liquid buffer, and activation of the linker film 22 for the purpose of facilitating binding of the ligand to the linker film 22. An example of an immobilizing method is the amine coupling method. An example of material for the linker film is carboxy methyl dextran, to bind an amino group contained in the ligand with the dextran directly by a covalent bond. An example of liquid for the activation is mixture of N'-(3-dimethylaminopropyl) carbodiimide hydrochloride (EDC) and N-hydroxy imide succinate (NHS). The sample immobilizing equipment 10, after the activation, introduces liquid buffer for the ligand immobilizing flow to wash and clean the flow channel 16.

Various liquids are available for use as the liquid buffer for the ligand immobilizing flow, and solvent or diluent for the ligand fluid 21. Examples of the liquids include buffer liquids, or physiological saline water and other aqueous solutions of physiological salts, and pure water. It is possible according to a type of the ligand to determine suitably solution types and pH values of the solutions, and types of substances to be mixed, and their density. If a biomaterial is used as a ligand, physiological saline water is used of which pH value is kept neutralized. In the amine coupling method described above, the linker film 22 is electrified negatively because of the carboxy methyl dextran. In consideration of this, it is possible to use phosphatic buffered saline (PBS) solution having strong operation of buffer and containing phosphate salt at high density which is not physiological, because protein can be electrified positively for the purpose of facilitating binding with the linker film 22.

The sample immobilizing equipment 10, after the activation and washing, introduces the ligand fluid 21 to the flow channel 16 for immobilization. Ligand 21a as sample such as biomaterial diffused in the ligand fluid 21, in introducing the ligand fluid 21, gradually migrates to and binds with the linker film 22. This is the ligand immobilizing flow of the ligand 21a on the sensing surface 13a. It is general that a step of the immobilization requires approximately one (1) hour, during which the sensor unit 12 is preserved in an environment conditioned suitably, for example at a conditioned temperature. Until the immobilization, the ligand fluid 21 in the flow channel 16 may be left to stand in a stationary state.

However, the ligand fluid 21 can be preferably stirred or turbulently flowed for ensured fluidity in the flow channel 16. The stirring or turbulent flow can promote binding of the ligand 21a with the linker film 22, to raise an immobilized amount of the ligand 21a.

When the immobilization of the ligand 21a on the sensing surface 13a is completed, the fluid dispenser draws and removes the ligand fluid 21 from the flow channel 16. Namely, the second pipette device 19b discharges the ligand fluid 21 by aspirating. After this, the sensing surface 13a is washed by introducing washing liquid into the flow channel 16. In the fluid dispenser, a blocking step is made after the washing. A blocking liquid is introduced into the flow channel 16, to deactivate the reaction group remaining without binding with the ligand. A preferable example of the blocking liquid is ethanol amine hydrochloride. After the blocking, the flow channel 16 is washed again. Then, the fluid dispenser introduces evaporation retardant to the flow channel 16, as will be described hereafter. The sensor unit 12 is left to stand until the assay, with the sensing surface 13a humid on the evaporation retardant.

For the assay, the sensor unit 12 is set in the assay apparatus 11. A plurality of dual pipette assemblies 26 are installed in the assay apparatus 11. Each of the dual pipette assemblies 26 includes a first pipette device 30 for aspiration and dispensation with a pipette tip, and a second pipette device 35 for aspiration with a pipette tip. The first pipette device 30 is used for delivery of fluid by aspiration at a reservoir, and then is set at the first orifice 16a, introduces the fluid to the flow channel 16.

For the assay in the assay apparatus, at first, liquid buffer is introduced into the flow channel 16, and caused to flow continuously for a prescribed time. After this, analyte solution or analyte fluid 27, as a fluid which contains analyte and fluid medium that may be solvent, is introduced into the flow channel 16. The measuring buffer is exited instead of filling of the analyte fluid 27. The analyte fluid 27 is kept stored in the flow channel 16 for a predetermined time, before liquid buffer is introduced again. Fluid used in the second orifice 16b, for example used analyte fluid and measuring buffer, is aspirated, drawn and recovered by the second pipette device 35. Note that the flow channel 16 may be cleaned or washed before initially introducing the liquid buffer.

Reading of data in a photo detector starts upon initially introducing the liquid buffer in order to detect a reference level of a signal. The reading is continued until the introduction of the liquid buffer at the second time after entry of the analyte fluid 27. It is possible not only to detect the reference level that is a base line, but to assay the interaction or reaction between the analyte and the ligand, and to measure a signal until dissociation between the analyte and ligand in response to introduction of the liquid buffer.

Various liquids are available for use as the liquid buffer for assay, and solvent or diluent for the analyte fluid 27. Examples of the liquids include buffer liquids, or physiological saline water and other aqueous solutions of physiological salts, and pure water. It is possible according to a type of a ligand or analyte to determine suitably solution types and pH values of the solutions, and types of substances to be mixed, and their density. To facilitate dissolving of the analyte, dimethyl sulfo-oxide (DMSO) can be added to the physiological saline water. The use of the DMSO considerably influences to a level of an output signal. The buffer for assay is used for detecting the reference level of the signal, as described above. If DMSO is contained in the fluid for the analyte, it is preferable to use buffer for assay at a DMSO density approximately equal to that of the fluid in the analyte.

In general, the analyte fluid 27 may be kept preserved for a long time, for example one (1) year. It is likely that a difference occurs between an initial level and a current level of the DMSO density owing to a change with time. If assay with high precision is required, such a difference in the density is estimated according to the reference signal (ref-signal) level upon introducing the analyte fluid 27, so that measured data can be compensated for by DMSO density compensation.

The reference signal or ref-signal is an output of the SPR derived from the reference region on the sensing surface 13a and free from immobilization of a ligand, and is a basis of comparison with a measuring signal. The measuring signal or act-signal is an output of the SPR derived from the measuring region on the sensing surface 13a and for immobilization of a ligand to react with an analyte. The data analyzer effects data analysis by obtaining data of a finite difference between the act-signal and ref-signal, and analyzes various items according to the finite difference. This makes it possible to cancel electric noise caused by external irregularities, such as individual specificity of the sensor unit 12 or the linker film 22 or the sensor cells 17, mechanical changes of the assay apparatus 11, temperature changes of the liquid, and the like. A signal with a high S/N ratio can be obtained.

Compensation data for the DMSO density compensation is obtained before introducing the analyte fluid 27. A plurality of liquid buffers different in the DMSO density are introduced to the sensor cells 17. Amounts of changes in the levels of ref-signal and act-signal are evaluated so as to obtain the compensation data.

An optical assay unit 31 is constituted by the illuminator 32 and a photo detector 33. The reaction between the ligand and analyte can be recognized as a change of a resonance angle, which is an angle of incidence of light received by the interface 13b. To this end, the illuminator 32 is caused to apply light to the interface 13b at various values of angles of incidence satisfying a condition of the total reflection. The illuminator 32 includes a light source 34 and an optical system 36, which includes a condensing lens, a diffusing plate and a polarizer. A position and angle of installation of those elements are so determined that an angle of incidence of the light satisfies the condition of the above total reflection.

Examples of the light source 34 include a light emitting diode (LED), laser diode (LD), super luminescent diode (SLD), and other light emitting element. A single element is used as the light source 34 as a point light source, to illuminate the interface 13b in a sensor cell. Note that, if simultaneous assay of plural sensor cells is desired, light from a single light source device may be separated into plural light paths for application to the sensor cells.

The diffusing plate diffuses light from the light source 34, and suppresses onset of irregularity in the light amount. The polarizer allows only p-polarized light to pass, the p-polarized light creating the surface plasmon resonance. Note that no polarizer is required if directions of rays emitted by the light source 34, for example an LD, are kept equal. However, a diffusing plate may be combined with the light source 34 of a type of which directions of emitted rays are kept equal. Directions of rays in polarization are changed to an unequal state by the passage through the diffusing plate. For this structure, the polarizer can be utilized to set equal the directions of the rays. The light obtained after the diffusion and polarization is condensed by a condensing lens, and directed to the prism 14. It is possible to travel rays with various angles of incidence toward the interface 13b without irregularity in the intensity.

The photo detector 33 detects intensity of received light reflected by the interface 13b. Light becomes incident upon the interface 13b at various angles of incidence. The interface 13b reflects the light at various reflection angles according to the incident angles. When reaction starts by the contact between the analyte and ligand, the resonance angle starts changes. An example of the photo detector 33 is a CCD area sensor or an array of photo diodes, which acquires changes in the reflection angle by detection of shifting the attenuation position of the reflected light on the photo reception surface. The photo detector 33 outputs and sends an SPR signal to the data analyzer. The data analyzer analyzes the SPR output from the assay apparatus 11, to recognize interaction between the analyte and ligand.

In FIGS. 1A and 1B, the illuminator 32 and the photo detector 33 are so depicted that a direction of incident light on to the sensor unit 12 and a direction of reflected light from the sensing surface 13a are parallel to a horizontal flow direction of the flow channel 16. However, this is for the simplicity of the illustration of the optical assay unit 31. Structurally, the illuminator 32 and the photo detector 33 are so disposed that a direction of incident light on to the sensor unit 12 and a direction of reflected light from the sensing surface 13a are perpendicular to a horizontal flow direction of the flow channel 16, namely an array direction of the sensor cells 17. See FIG. 4. Also, the optical assay unit 31 may be constructed exactly as illustrated in FIGS. 1A and 1B.

Figure 2:
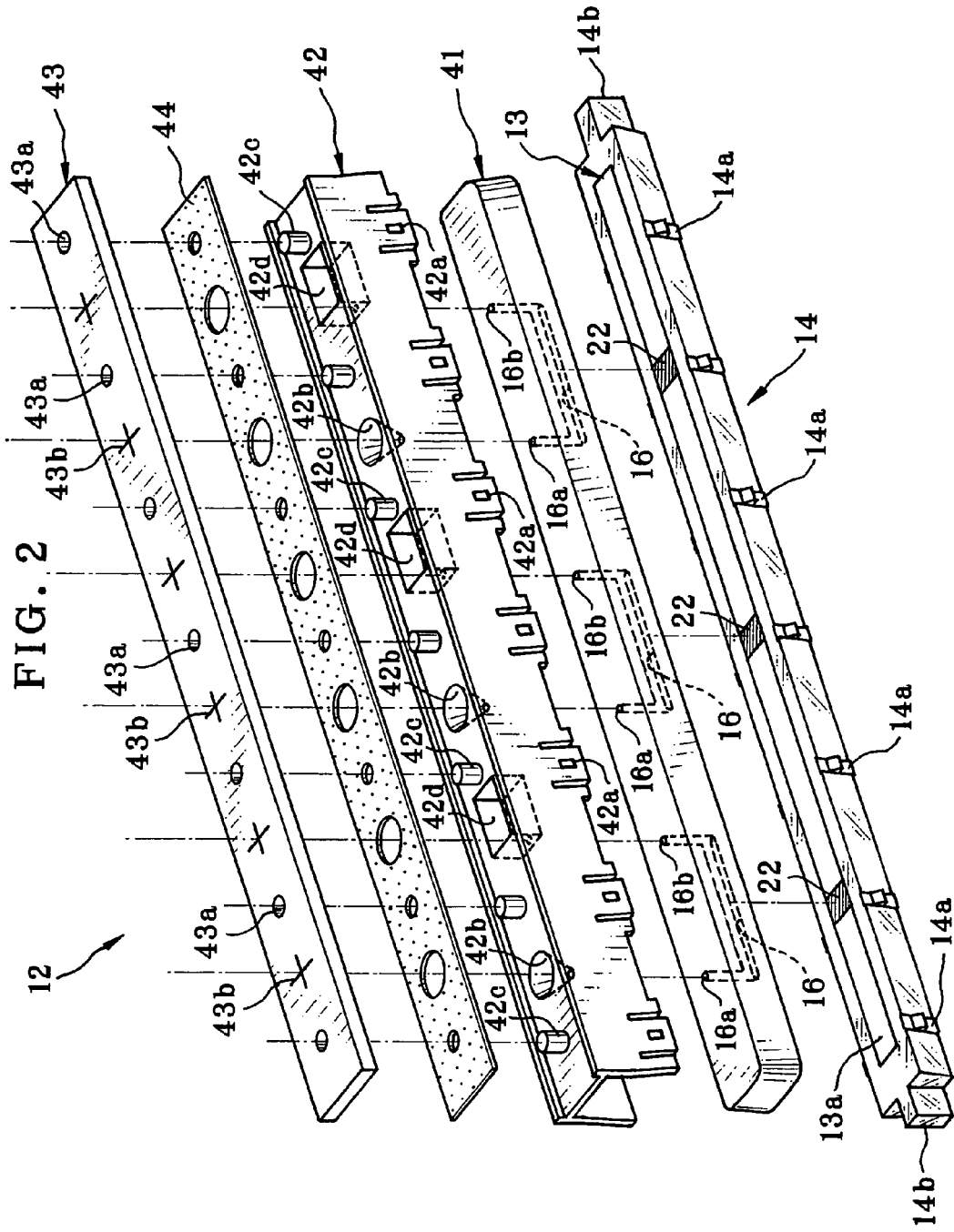
FIG. 2 is a perspective view illustrating a sensor unit.

In FIG. 2, the sensor unit 12 is illustrated structurally. The sensor unit 12 includes a flow cell 41, the prism 14, a sealing block 42, and a flow cell lid 43. The flow cell 41 has the three flow channels 16 formed through the same, or at least one flow channel. The prism 14 is dielectric, and is overlaid with the thin film 13 on its upper surface. The sealing block 42 keeps the flow cell 41 positioned by fitting its lower surface on the upper surface of the prism 14. The flow cell lid 43 is disposed higher than the sealing block 42.

The number of the flow channels 16 is three in the flow cell 41. The flow cell 41 extends in one direction, in which the flow channels 16 are arranged. The flow channels 16 constitute the sensor cells 17 together with the thin film 13 in connection with its lower surface. See FIGS. 1A and 1B. The flow cell 41 is formed from elastic material for the purpose of ensuring tightness in contact with the thin film 13. Examples of elastic materials include rubber, polydimethylsiloxane (PDMS), and the like. When the lower surface of the flow cell 41 is pressed on an upper surface of the prism 14, the flow cell 41 is elastically deformed, to remove a space between its surface and the thin film 13. Open lower portions of the flow channels 16 are closed fluid-tightly by the upper surface of the prism 14. Note that, in the sensor unit 12, the number of the flow channels 16 may not be three, but can be one or two, or four or more.

The thin film 13 is formed by vapor deposition on the prism 14. The thin film 13 of a strip shape is positioned on a train of the flow channels 16. Also, the linker film 22 is formed on the upper surface of the thin film 13 for the flow channels 16. Retention claws 14a are formed to project from the prism 14 at its sides as viewed longitudinally. Retention tabs 42a of the sealing block 42 are engageable with the retention claws 14a. The flow cell 41 is sandwiched between the sealing block 42 and the prism 14. A lower surface of the flow cell 41 is kept fitted on the prism 14. A single component including the flow cell 41, the thin film 13 and the prism 14 is obtained.

Positioning projections 14b protrude from ends of the prism 14 as viewed in its longitudinal direction. A sensor holder (not shown) contains a plurality of sensor units 12 in the course of the sample immobilizing flow. The positioning projections 14b are formed for positioning the sensor unit 12 in a contained state by engagement with the sensor holder.

A passage aperture 42b is formed in the sealing block 42, and positioned at the first orifice 16a of the flow channel 16, for entry of an end of a pipette device. The passage aperture 42b has a funnel shape with a decreasing diameter for introducing liquid ejected by the pipette toward the first orifice 16a. A lower face of the passage aperture 42b is connectable with the first orifice 16a of the flow channel 16 for flow of fluid with the sealing block 42. A fluid reservoir chamber 42d is formed in the sealing block 42, positioned at the second orifice 16b of the flow channel 16, and reserves fluid flowing out of the second orifice 16b after passage in the flow channel 16. The fluid reservoir chamber 42d prevents scattering of the fluid about the sensor unit 12 from the second orifice 16b in a temporary manner. For the immobilization, the second pipette device 19b is inserted in the fluid reservoir chamber 42d. For the assay, the second pipette device 35 is inserted in the fluid reservoir chamber 42d. Fluid in the fluid reservoir chamber 42d is drawn and aspirated for recovery.

Furthermore, it is possible in the sample immobilizing flow to keep ligand fluid in the fluid reservoir chamber 42d, and to cause the same to flow back to the flow channel 16, for repeated introduction of the ligand fluid to the sensing surface 13a. This is effective in raising efficiency in the immobilization, because of high fluidity of the ligand fluid in the flow channel 16.

When the sealing block 42 is engaged with the prism 14 together with the flow cell 41, a lower opening of the passage aperture 42b is connected with the first orifice 16a of the flow channel 16. The fluid reservoir chamber 42d is connected with the second orifice 16b.

Rod shaped bosses 42c are formed to project beside the passage aperture 42b. Positioning holes 43a are formed in the flow cell lid 43. The bosses 42c are fitted in the positioning holes 43a, to position the flow cell lid 43 firmly. Double sided adhesive tape 44 attaches the flow cell lid 43 to an upper surface of the sealing block 42. Note that suitable holes are formed in the double sided adhesive tape 44, and associated with the passage aperture 42b and the bosses 42c.

The flow cell lid 43 covers the passage aperture 42b and the fluid reservoir chamber 42d communicating to the flow channel 16, and prevents evaporation of liquid in the flow channel 16. The flow cell lid 43 is formed from rubber, elastomer, resin or other elastic material. A cross shaped slit 43b is formed in the flow cell lid 43 and positioned respectively at the passage aperture 42b and the fluid reservoir chamber 42d. The flow cell lid 43 is required to cover the passage aperture 42b and the fluid reservoir chamber 42d in order to prevent liquid in the flow channel 16 from evaporation. However, no pipette can enter the passage aperture 42b and the fluid reservoir chamber 42d if covering of the flow cell lid 43 is complete. So the cross shaped slit 43b is formed to enable insertion of pipettes, and to close the passage aperture 42b and the fluid reservoir chamber 42d while no pipette is inserted. If a pipette is forcibly pressed into the cross shaped slit 43b, its edges are elastically deformed, to allow receipt of the pipette by becoming open. When the pipette is externally pulled out, the cross shaped slit 43b elastically closes the passage aperture 42b and the fluid reservoir chamber 42d again by returning to its initial state.

Figure 3:
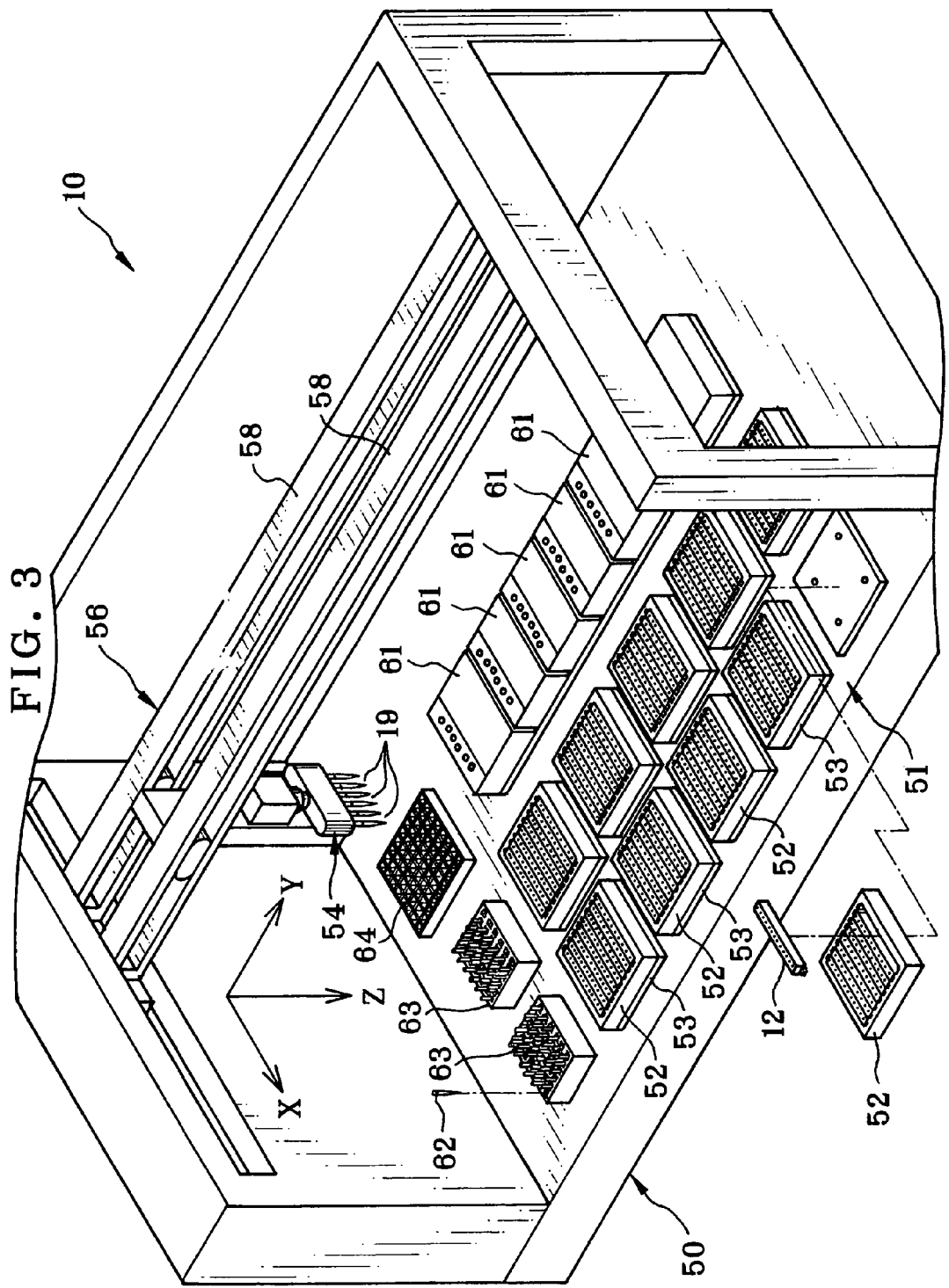
FIG. 3 is a perspective view illustrating sample immobilizing equipment.

In FIG. 3, the sample immobilizing equipment 10 has a casing or base 50 and an immobilizing stage 51 for placement. The immobilizing stage 51 is a support with a space for the sensor unit 12. The sensor unit 12, while placed on the immobilizing stage 51, is processed for every step included in the sample immobilizing flow and immobilization. The immobilizing stage 51 is a sample immobilizing stage for the sensor unit 12.

Figure 5:
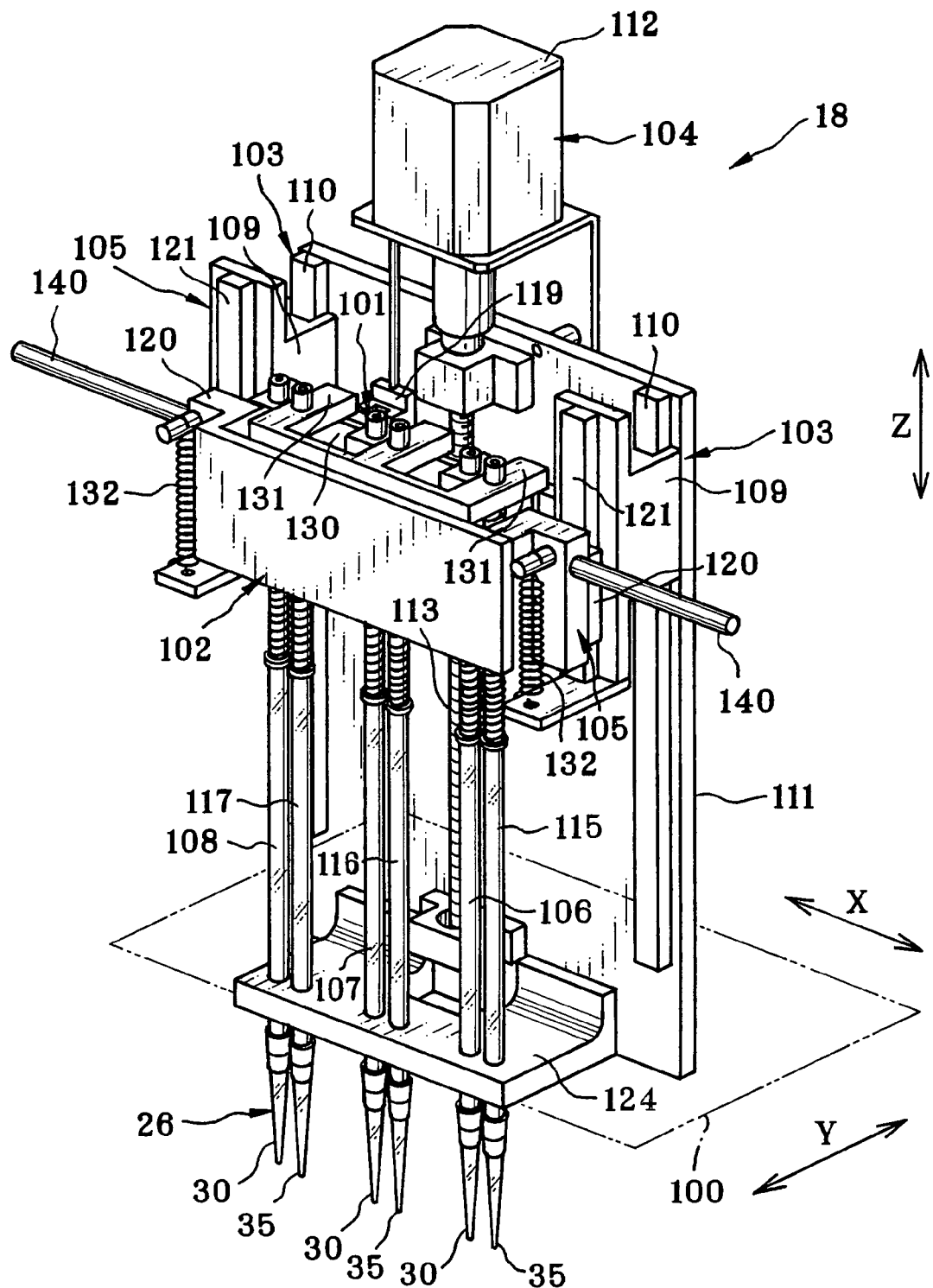
FIG. 5 is a perspective view illustrating a fluid dispenser.

A sensor holder 52 contains a plurality of the sensor unit 12, and is loaded in the sample immobilizing equipment 10. The number of the sensor unit 12 containable in the sensor holder 52 is eight, but may be changed suitably. Positioning portions are formed in the sensor holder 52, and engageable with the positioning projections 14b of the sensor unit 12 for positioning the sensor unit 12. A lower panel of the sensor holder 52 has a lower opening between support portions for supporting ends of the sensor unit 12. To remove the sensor unit 12 from the sensor holder 52 in the assay step, a pusher 81 of FIG. 5 is inserted through the lower opening to push up the sensor unit 12.

In the immobilizing stage 51 are arranged a plurality of pallets or supports 53, for example 10, for supporting the sensor holder 52 placed adjacently. Positioning bosses are formed on the pallets 53 for positioning the sensor holder 52.

A pipette head 54 is included in the sample immobilizing equipment 10, and associated with three dual pipette assemblies 19. The pipette head 54 accesses the sensor unit 12 disposed in the immobilizing stage 51, and dispenses and draws fluid. With the three dual pipette assemblies 19, the pipette head 54 can simultaneously access the of the sensor cells 17 included in the sensor unit 12 for dispensation and drawing of fluid. A controller (not shown) is incorporated in the sample immobilizing equipment 10, and controls parameters for each of the pipette head 54 in relation to the dual pipette assembly 19 in aspiration and dispensation, the parameters including amounts of aspiration and dispensation, and scheduling of aspiration and dispensation.

A pipette head shifter 56 is disposed on the casing 50 for shifting the pipette head 54 in three directions of X, Y and Z. The pipette head shifter 56 is a moving device and may include a conveyor belt, pulleys, a carriage and a motor. The pipette head shifter 56 includes a lifter, a first shifting mechanism, and a second shifting mechanism. The lifter moves the pipette head 54 up and down. The first shifting mechanism includes a guide rail 58 for supporting the lifter movably, and shifts the pipette head 54 with the lifter in the Y direction. The second shifting mechanism has two portions for supporting ends of the guide rail 58, and shifts the pipette head 54 with the guide rail 58 in the X direction. The pipette head shifter 56 is controlled by a controller, and driven to control the position of the pipette head 54 in the horizontal and vertical directions.

Plural fluid storages or reservoirs 61 are placed on the casing 50 for storing various fluids for flow into the flow channel 16, such as ligand fluid, washing liquid, buffer liquid for immobilization, evaporation retardant, activation fluid, and blocking liquid. The number of the fluid reservoirs 61 may be determined according to the number of kinds of fluids. Six insertion openings are formed and arranged in each of the fluid reservoirs 61. The number and pitch of the insertion openings are determined according to the number of the pipette nozzles in the pipette head 54 and their pitch of arrangement. To introduce fluid into the sensor cells 17, the pipette head 54 accesses the fluid reservoirs 61 to aspirate required fluids, and then shifts to the immobilizing stage 51 to introduce the fluids to the sensor unit 12.

A pipette tip storage 63 is disposed on the casing 50, and stores pipette tips 62' in a pipette device for replacement. Pipette tips are fitted on ends of pipette nozzles of respectively the pipette devices of the dual pipette assembly 19 in a removable manner. The pipette tips are detipped for replacement so as to prevent mixture and contamination of plural liquids in the pipette tips in direct contact with flowing liquid. A pickup and release mechanism (not shown) for automatic detipping is associated with the pipette devices. To renew the pipette tips, the pipette head 54 moves to a discarding receptacle (not shown), so the pipette tips are released after being used. Then the pipette head 54 moves to the pipette tip storage 63, and picks up and sets unused pipette tips 62 on the pipette nozzles.

There is a multi well plate 64 or fluid reservoir, having a plurality of wells with an equally formed opening and arranged in a matrix form. Objects of the multi well plate 64 are to store fluid temporarily after aspiration with a pipette device, and to mix a plurality of fluids. The multi well plate 64 is structurally the same as a multi well plate 88 for storing analyte fluid.

To start immobilization, the casing of the sample immobilizing equipment 10 is covered by a cover (not shown), to shield the inside of the sample immobilizing equipment 10 having the immobilizing stage 51 from the outside. A temperature adjuster (not shown) is associated with the sample immobilizing equipment 10 to keep the temperature adjustable in the sample immobilizing equipment 10. After introduction of the ligand in the sensor cells 17, the sensor unit 12 is kept on the immobilizing stage 51 to stand for a predetermined time until completion of immobilization of the ligand 21a on the sensing surface 13a. During the storage, the ligand fluid 21 in the flow channel 16 is stirred or turbulently flowed as required. Degree of immobilization depends on temperature or other environmental factors of the sensor unit 12. The temperature adjuster keeps the inner temperature of the sample immobilizing equipment 10 at a predetermined level. The target temperature and time for storage are suitably determined according to a type of the ligand 21a.

When the immobilization is completed, liquid buffer is introduced into the sensor cells 17. The first pipette device 19a is inserted into the cross shaped slit 43b and introduced to the sensor cells 17 having been filled with the ligand fluid. When the buffer is introduced to the flow channel 16 through the first orifice 16a, ligand fluid is caused to flow toward the second orifice 16b and exited from the flow channel 16 by pressure of the buffer. The second pipette device 19b operates for aspiration in synchronism with introduction of the first pipette device 19a, and draws the buffer for removal. Thus, the content in the sensor cells 17 is substituted.

After the washing, evaporation retardant is introduced into the sensor cells 17 for preventing drying of the ligand 21a. At the same time, liquid buffer is caused to flow and exited from the flow channel 16 by pressure of the evaporation retardant and by aspiration in synchronism with introduction of the evaporation retardant. Thus, the content in the sensor cells 17 is substituted. The sensor unit 12 after the substitution, the sensor holder 52 with the sensor unit 12 is transferred to the assay apparatus 11 with the sensing surface 13a wet in the evaporation retardant with the ligand 21a. The ligand can be kept free from being dry until the start of assay.

Various liquids are available for use as the evaporation retardant. Examples of the liquids include buffer liquids, or physiological saline water and other aqueous solutions of physiological salts, and pure water. It is possible according to a type of the ligand to determine suitably solution types and pH values of the solutions, and types of substances to be mixed, and their density. An amount of the evaporation retardant is sufficient if the ligand 21a on the thin film 13 can be humid by the evaporation retardant. However, an evaporating amount of the evaporation retardant should be considered. An amount of the evaporation retardant should be increased. For example, the flow channel 16 may be filled with fluid.

Figure 4:
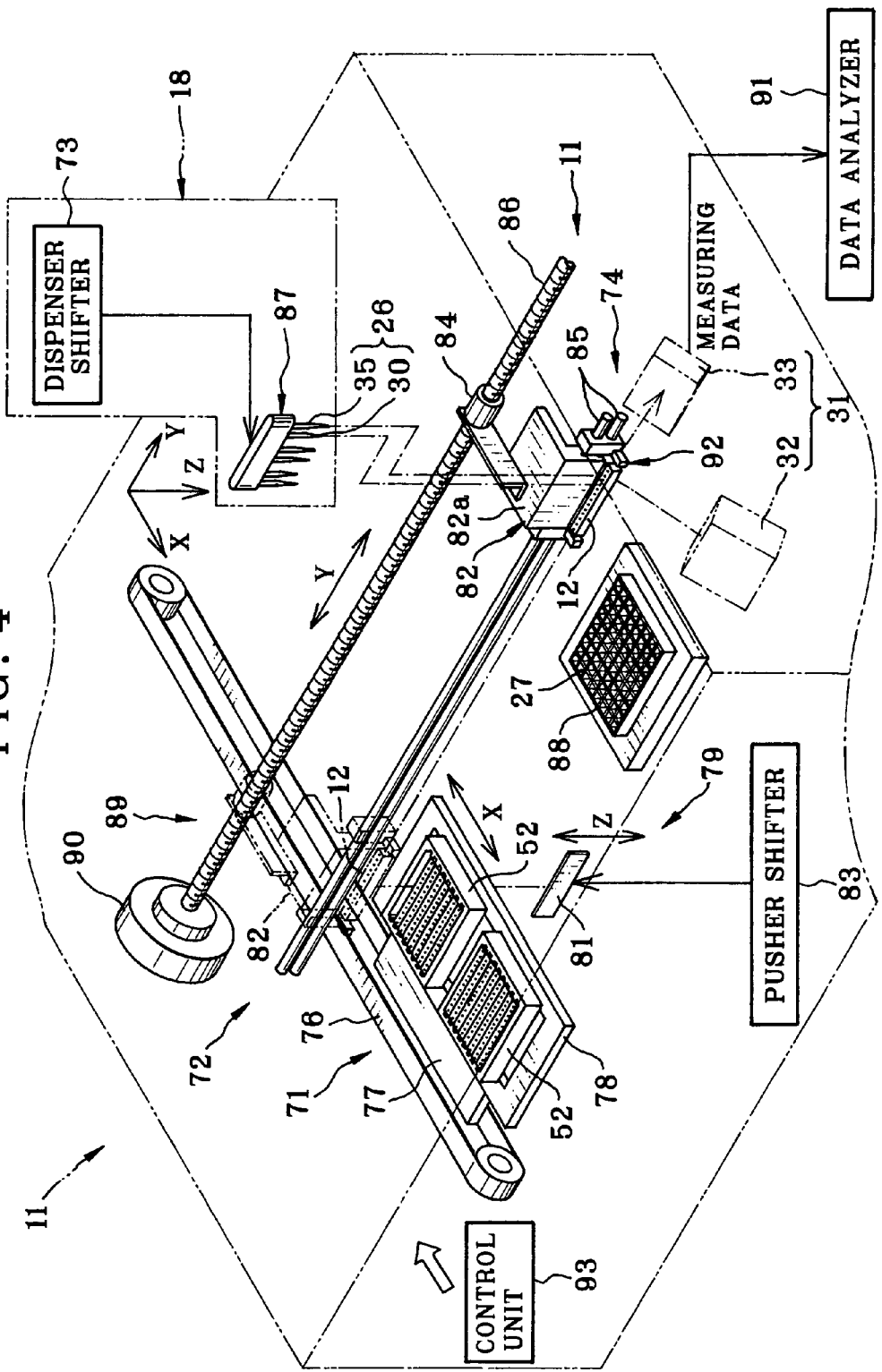
FIG. 4 is a perspective view illustrating an assay apparatus.

In FIG. 4, the assay apparatus 11 is constituted by a holder shifter 71, a pickup mechanism 72, a multi channel fluid dispenser 18 and an assay stage 74. The holder shifter 71 includes a conveyor belt 76, a carriage 77 and a support plate 78. The carriage 77 is secured to the conveyor belt 76. The support plate 78 is secured to the carriage 77, and supports the sensor holder 52 with a plurality of the sensor units 12 after the immobilization. The holder shifter 71 moves the support plate 78 in the X direction with the sensor holder 52 to shift the sensor unit 12 to the standby stage. Thus, the sensor unit 12 from the sensor holder 52 is set in the standby stage in an orientation to extend perpendicularly to the X direction of shifting of the holder shifter 71 for the support plate 78.

The pickup mechanism 72 includes a sensor handler 79 and a transporting mechanism 89. The sensor handler 79 pushes up the sensor unit 12 from the standby position to a clamping position. The transporting mechanism 89 squeezes the sensor unit 12 raised by the sensor handler 79, and transports the sensor unit 12 to the assay stage 74. The sensor handler 79 includes the pusher 81 and a pusher shifter 83. The pusher 81 is moved up and down in the Z direction by the pusher shifter 83. The sensor holder 52, as described above, has a lower opening. The support plate 78 has openness associated with the lower opening. The pusher 81 moves through the support plate 78 and enters the lower opening in the sensor holder 52, and comes up toward a lower face of the sensor unit 12. The pusher 81 keeps the sensor unit 12 stable without fall, and raises the sensor unit 12 from the standby stage to the clamping position.

The transporting mechanism 89 includes a handler or handling head 82 and a moving unit for moving the handler 82 between a clamping position and the assay stage 74. The moving unit includes a nut 84, guide rods 85, a screw 86, a motor 90, a position detector, and a control unit 93. The handler 82 includes a handler body or carriage 82a and a clamping mechanism 92. The clamping mechanism 92 is associated with the handler body 82a, and handles the sensor unit 12. The motor 90 causes the screw 86 to rotate forwards and backwards. The screw 86 extends in the Y direction perpendicular to the X direction. The nut 84 is caused by rotation of the screw 86 to move in its axial direction according to the lead of the threads of the screw 86. The handler body 82a has the nut 84 in a firmly secured manner. The guide rods 85 extend in the Y direction, and keeps slidable the handler body 82a without rotational shift.

The position detector (not shown) includes a detection projection and a position sensor. The detection projection projects from the handler body 82a. The position sensor is a U-shaped photo sensor disposed each of the clamping position and the assay stage. A signal output by the position sensor upon detecting the detection projection is sent to the control unit 93. The control unit 93 monitors signals from the position sensors, and controls rotation of the motor 90, and also controls synchronization of the holder shifter 71, the pickup mechanism 72, a dispenser shifter 73 and the optical assay unit 31.

A rotary encoder is connected with an output shaft of the motor 90. The control unit 93 can monitor a position of movement of the handler body 82a according to a pulsed signal from the rotary encoder. This fine control is effective in precisely advancing the handler body 82a to a selected one of assay positions from the home position where the detection projection is detected by a position sensor in the assay stage. Note that a stepping motor may be used in place of the position detector or rotary encoder. Factors related to the motor may be controlled according to pulses input to the stepping motor, the factors including a rotational angle, rotational direction, rotational speed or the like of the motor.

As described above, a direction of incident light on to the sensor unit 12 and a direction of reflected light from the sensing surface 13a are perpendicular to a horizontal flow direction of the flow channel 16, namely an array direction of the sensor cells 17.

The multi channel fluid dispenser 18 includes a multi channel dispensing head or dispenser carriage 87 and the dispenser shifter 73. The multi channel dispensing head 87 includes the first and second pipette devices 30 and 35. One dual pipette assembly is constituted by the first and second pipette devices 30 and 35. The three dual pipette assemblies are arranged in the multi channel dispensing head 87. The multi channel dispensing head 87 comes to a selected one of plural positions for dispensing or aspirating fluid. Three dual pipette assemblies 19 are included in the multi channel dispensing head 87, simultaneously to dispense or aspirate fluid at the three sensor cells 17 in the sensor unit 12. Positions where the multi channel dispensing head 87 is settable include a measuring buffer aspirating position, analyte fluid aspirating position, assay position, and detipping position.

A multi well plate for storing measuring buffer is disposed in the measuring buffer aspirating position. A multi well plate 88 for storing the analyte fluid 27 is disposed in the analyte aspirating position. The multi well plate 88 includes wells arranged in a matrix form in two dimensional manner of X and Y directions. Each of the wells contains fluid. For example, the multi well plate 88 disposed in the fluid aspirating position contains a pluralities of kind of the analyte fluid 27.

When the sensor unit 12 is shifted to the assay position, the dispenser shifter 73 shifts the multi channel dispensing head 87 to one of the measuring buffer aspirating position or the analyte fluid aspirating position, and to the sensor unit 12 in the assay position. The multichannel dispensing head 87 accesses the sensor cells 17 for dispensation and removal of fluid. Two pipette nozzles are included in the multi channel dispensing head 87. Pipette tips constituting the first and second pipette devices 30 and 35 are fitted on ends of the pipette nozzles. In the measuring buffer aspirating position or analyte fluid aspirating position, the second pipette device 35 is caused to access and draw measuring buffer or analyte fluid from the multi well plate. In the assay position, a specific one of the sensor cells 17 is accessed by the first and second pipette devices 30 and 35 for dispensing and aspirating fluid.

Pipette tip storage (not shown) is disposed in a detipping position for storing unused pipette tips as spare. At each time after introduction or drawing of fluid, the dispenser shifter 73 causes the multi channel dispensing head 87 to the detipping position, to replace the pipette tips at the pipette nozzles. This is structurally the same as that in the sample immobilizing equipment 10.

The sensor unit 12 includes a plurality of the sensor cells 17. The transporting mechanism 89 in the assay stage 74 shifts the sensor unit 12 finely in the Y direction at a pitch of the sensor cells 17, and positions each of the sensor cells 17 at the assay point in the path of light from the illuminator 32.

For assay, the multi channel dispensing head 87 accesses the multi well plate 88 for the first pipette devices 30 with the pipette tips 62 to aspirate and draw the analyte fluid 27. Then the first pipette devices 30 are shifted to the assay stage 74 to introduce the analyte fluid 27 to the sensor cells 17 in the assay position. The sensor unit 12 transferred from the sample immobilizing equipment 10 contains evaporation retardant in the sensor cells 17 until start of assay in the assay apparatus 11. Measuring buffer is introduced upon the start of assay into the sensor cells 17 by the first pipette devices 30, and causes the evaporation retardant to exit from the sensor cells 17. The evaporation retardant is aspirated by the second pipette device 35 through the pipette tip 62.

Note that the measuring buffer is preferably introduced for plural times at the time of removing the evaporation retardant from the flow channel 16. If the measuring buffer is introduced at only one time, failure may occur in removal of the evaporation retardant from the flow channel 16, to leave its residual content in the flow channel 16. When the measuring buffer is introduced for two or more times, residual content can be reduced in the flow channel 16.

Measuring data acquired by the photo detector 33 is transmitted to the data analyzer 91. The data analyzer 91 analyzes interaction between the analyte and ligand according to the measuring data.

Figure 6:
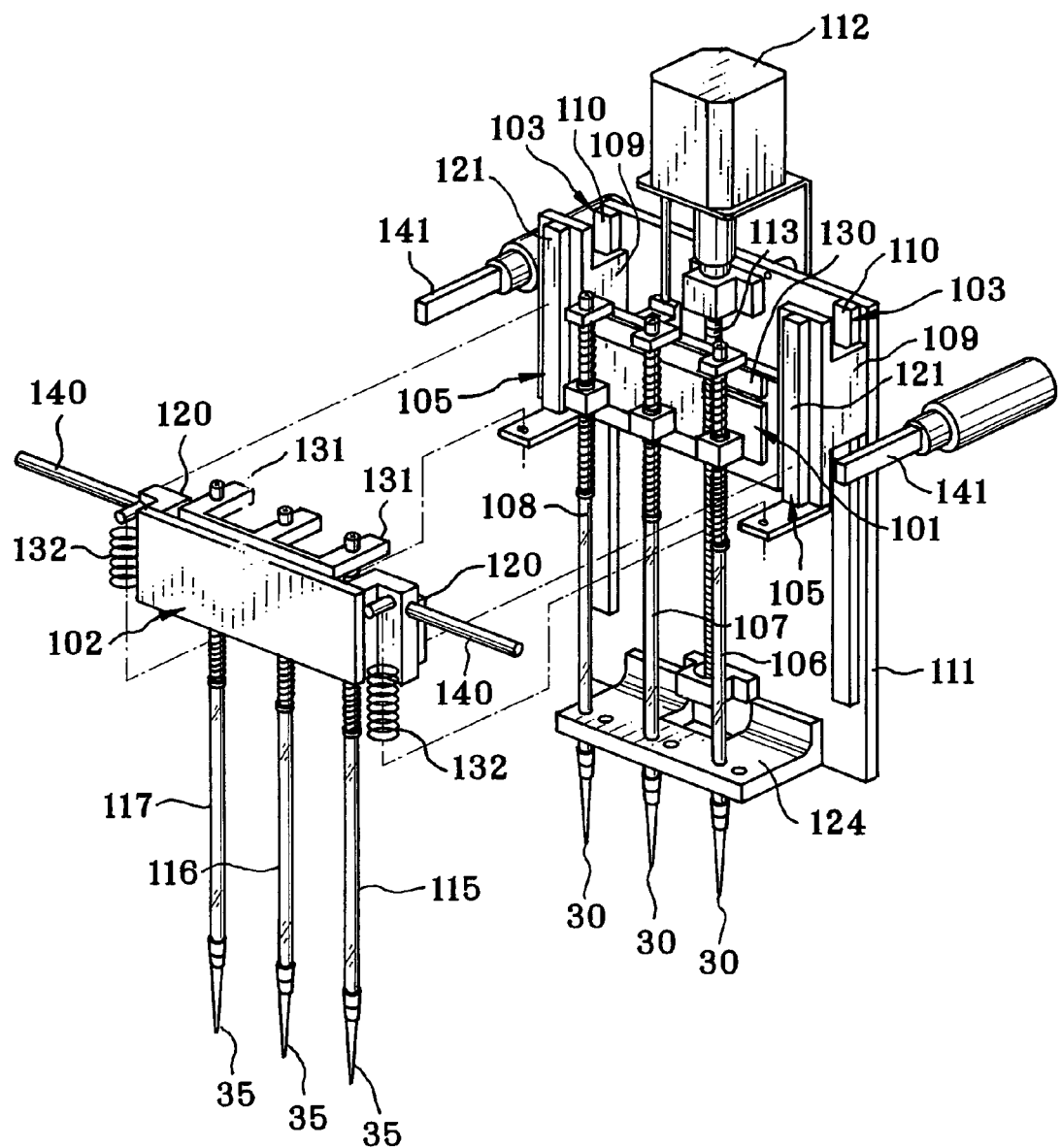
FIG. 6 is an exploded perspective view illustrating the fluid dispenser.

In FIG. 5, a dispenser table for a moving unit 100 supports the multi channel fluid dispenser 18. Also as depicted in FIG. 6, the multi channel fluid dispenser 18 includes a first pipette head 101, a second pipette head 102, a first guide mechanism 103, a driving mechanism 104, and a second guide mechanism 105. The multi channel dispensing head 87 is constituted by the first and second pipette heads 101 and 102. The dispenser shifter 73 includes the moving unit 100 for the X and Y direction, the first guide mechanism 103, the driving mechanism 104, and the second guide mechanism 105.

In the first pipette head 101 are arranged three pipette nozzles 106, 107 and 108 for aspiration and dispensation, which constitute the first pipette device 30 with a removable pipette tip. The first guide mechanism 103 guides the first pipette head 101 vertically in the Z direction, and includes a slidable projection 109 and a slide rail ridge 110 or guide rail as slide rail portion. The slidable projection 109 is disposed on the first pipette head 101. The slide rail ridge 110 is engaged with the slidable projection 109. A support frame 111 has the slide rail ridge 110 secured thereto or formed thereon.

Figure 7:
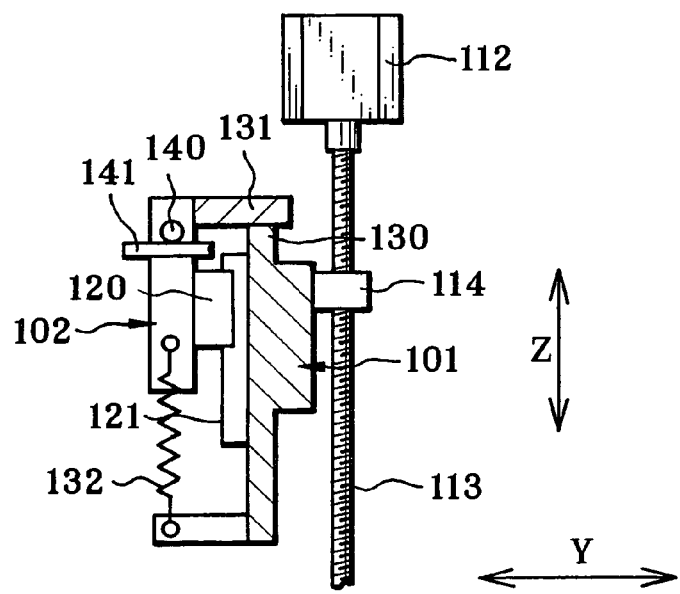
FIG. 7 is a front elevation illustrating a relationship between first and second pipette heads in a vertical direction.
Figure 8:
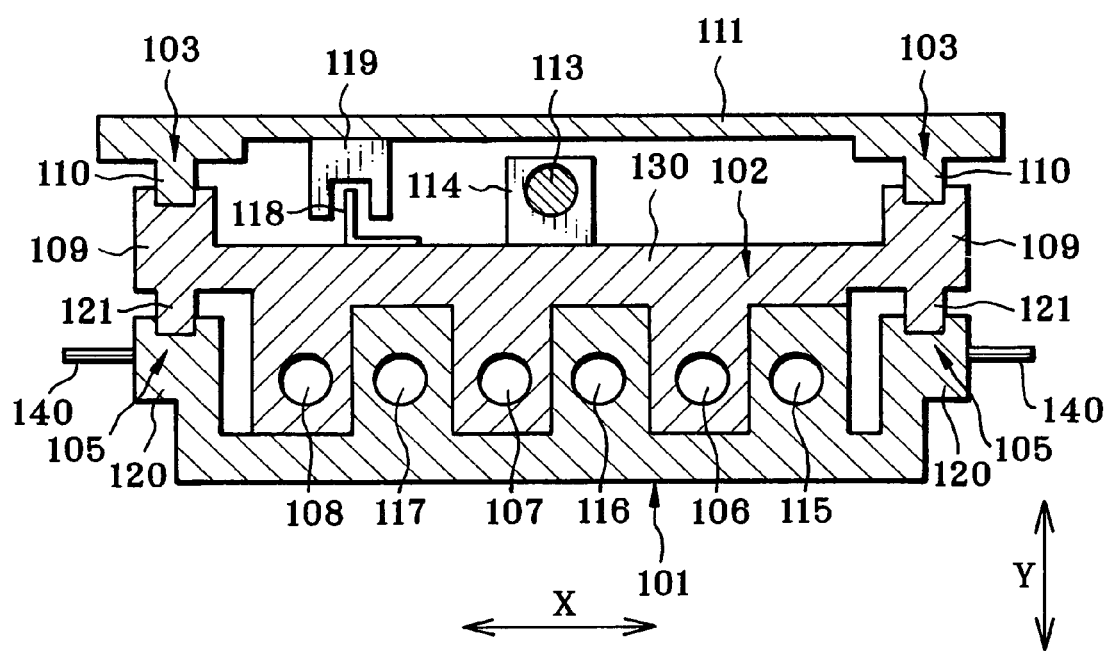
FIG. 8 is a horizontal section illustrating a relationship between the first and second pipette heads in a horizontal direction.

The driving mechanism 104 includes a Z direction motor 112, a threaded rod 113 for transmission, and a nut fitted carrier support 114 as a nut portion. The Z direction motor 112 is controllable for the rotational angle according to energy applied thereto, for example a servo motor or stepping motor. The threaded rod 113 is rotated by the Z direction motor 112. The nut fitted carrier support 114 is engageable with the threaded rod 113. In FIGS. 7 and 8, the nut fitted carrier support 114 is fixedly positioned on the first pipette head 101. The threaded rod 113 extends in parallel with the slide rail ridge 110. The driving mechanism 104 drives the Z direction motor 112, and moves the first pipette head 101 in the sliding direction of the first guide mechanism 103. The first pipette head 101 is movable between a lower position and an upper position higher than the lower position for retraction.

A detection projection 118 of a panel shape protrudes from the first pipette head 101. A position sensor 119 is secured to the support frame 111, and detects the detection projection 118 when the first pipette head 101 comes to an upper home position. A detection signal from the position sensor 119 is transmitted to a controller which will be described later. The controller receives the detection signal, and responsively causes the driver to stop the Z direction motor 112. Lower positions for stop are different according to the measuring buffer aspirating position, analyte fluid aspirating position, assay position, and detipping position. The controller sends the Z direction motor 112 pulse signals predetermined for access to those positions, and sets the multi channel dispensing head 87 in a well positioned manner for one of lower positions different between those.

In the second pipette head 102 are arranged three aspiration pipette nozzles 115, 116 and 117, which constitute the second pipette device 35 with a removable pipette tip. The second guide mechanism 105 guides the second pipette head 102 vertically in the Z direction relative to the first pipette head 101, and includes a slidable projection 120 and a slide rail ridge 121 or guide rail as slide rail portion. The slide rail ridge 121 is engaged with the slidable projection 120. The slide rail ridge 121 is secured to or projects from the first pipette head 101. The slidable projection 120 is fixed on the second pipette head 102. Also, a support panel 124 is disposed to project from the support frame 111, and includes six (6) sliding through holes, where the pipette nozzles 106-108 and the aspiration pipette nozzles 115-117 are inserted in a slidable manner.

Note that pumps (not shown) are respectively connected with the pipette nozzles 106-108 in the first pipette head 101. Pumps (not shown) are respectively connected with the aspiration pipette nozzles 115-117 of the second pipette head 102. The pumps are actuated to cause the pipette nozzles 106-108 and the aspiration pipette nozzles 115-117 to aspirate or dispense fluid through the first or second pipette device 30 or 35.

In FIG. 7, a stopper 130 is formed with the first pipette head 101. There is a contact projection 131 as a contact portion on the second pipette head 102. The stopper 130 contacts the contact projection 131 upwards at such a height where the pipette tip of the second pipette device 35 is as high as that of the first pipette device 30. The stopper 130 keeps the second pipette head 102 from moving down. Biasing tension coil springs 132 are connected between the first and second pipette heads 101 and 102 for biasing those in a direction toward each other in the Z direction. The tension coil springs 132 bias the second pipette head 102 to cause the contact projection 131 to contact the stopper 130. Even when the first pipette head 101 moves down, the tension coil springs 132 cause the second pipette head 102 to move together with the first pipette head 101 by the contact of the stopper 130 with the contact projection 131.

Figure 13:
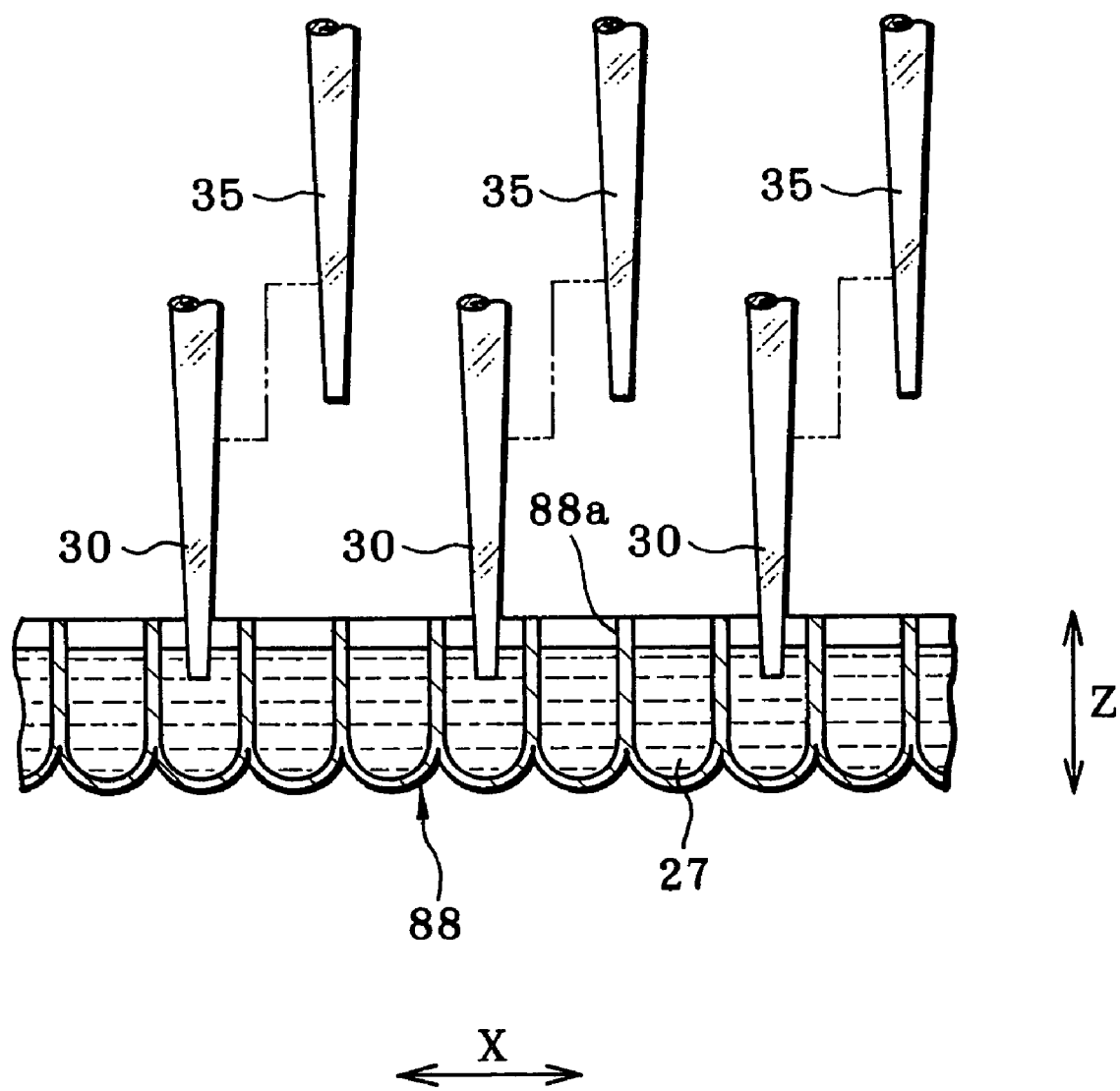
FIG. 13 is a front elevation illustrating shifting down only the first pipette device for aspiration.

In FIG. 8, portions of a comb tooth shape are formed with each of the first and second pipette heads 101 and 102, and support the pipette nozzles 106-108 and the aspiration pipette nozzles 115-117. Those can be arranged in one line and supported in an alternate manner. An interval from the pipette nozzles 106-108 to the aspiration pipette nozzles 115-117 is set equal to an interval between the first and second orifices 16a and 16b of the flow channel 16. An interval in the dual pipette assembly 26 is equal to that of the flow channel 16, namely that between one of the pipette nozzles 106-108 and an associated one of the aspiration pipette nozzles 115-117. Wells 88a in the multi well plate 88 of FIG. 13 are arranged at an interval equal to that of the pipette nozzles 106-108.

The second pipette device 35 or the second pipette head 102 does not require moving down in the measuring buffer aspirating position and the analyte fluid aspirating position, because of aspirating of fluid through the first pipette device 30. In FIGS. 5 and 6, two blocking projecting rods 140 in a blocking mechanism protrude from sides of the second pipette head 102. Two stopper rods 141 in the blocking mechanism is disposed stationarily in the measuring buffer aspirating position and the analyte fluid aspirating position for engagement with the blocking projecting rods 140. It is to be noted that any form may be used for engagement with the stopper rods 141 in place of the blocking projecting rods 140, for example a recess in the second pipette head 102.

Figure 9:
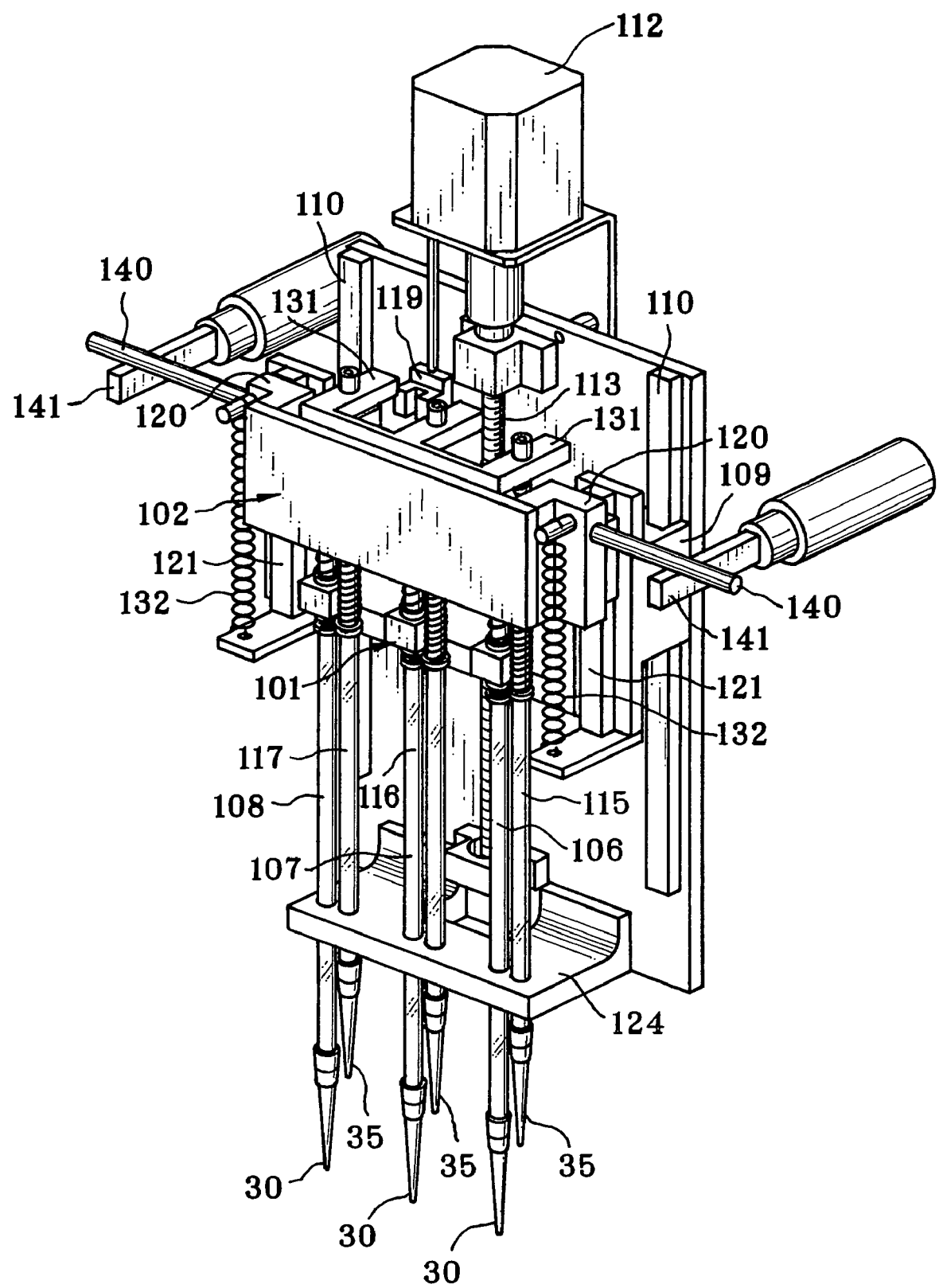
FIG. 9 is a perspective view illustrating a state of shifting down only the first pipette head in the assay position.
Figure 10:
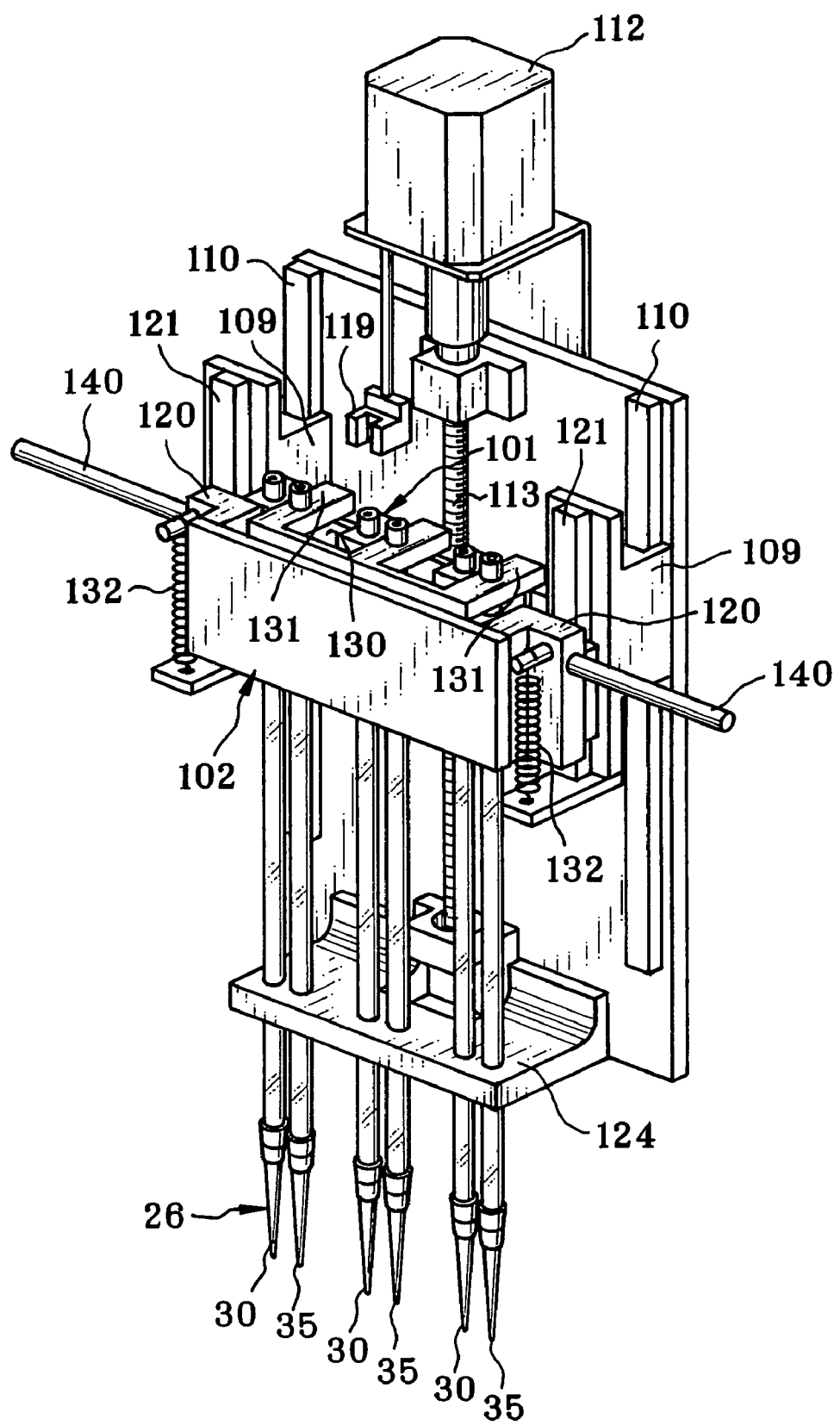
FIG. 10 is a perspective view illustrating shifting down of the second pipette head in compliance with that of the first pipette head.

The multi channel dispensing head 87 is moved only by the moving mechanism of the X and Y directions, and comes to any one of the measuring buffer aspirating position, analyte aspirating position and the like. The first pipette head 101 is in the upper home position in the Z direction. When movement of the first pipette head 101 is completed in the X and Y directions, the stopper rods 141 become engaged with the blocking projecting rods 140 in the upward direction. Note that the stopper rods 141 may be disposed at a height with a space from the blocking projecting rods 140. The Z direction motor 112 is driven to move down the first pipette head 101. As illustrated in FIG. 9, the second pipette head 102 is stopped by the stopper rods 141 from moving down. So only the first pipette head 101 moves down. In the assay position, none of the stopper rods 141 is disposed as illustrated in FIG. 10. The Z direction motor 112 is driven to move down the first pipette head 101. The second pipette head 102 also moves down together with the first pipette head 101.

The support frame 111 supports the multi channel dispensing head 87, the first guide mechanism 103, the second guide mechanism 105 and the driving mechanism 104. The moving unit 100 for the X and Y directions includes two motors, and moves the support frame 111 in the X and Y directions in a synchronized manner. In the drawing, the moving unit 100 is depicted in a simplified manner.

In FIG. 11, there is a controller 150 with which motor drivers 156, 157 and 158 and pump drivers 159 and 160 are connected. A first pump 151 for aspiration and dispensation and a second pump 152 for aspiration are driven by the pump drivers 159 and 160. An X direction motor 153, a Y direction motor 154 and the Z direction motor 112 are driven by the motor drivers 156-158. The position sensor 119 detects the upper home position of the first pipette head 101, and used for controlling the Z direction motor 112.

Figure 12A:
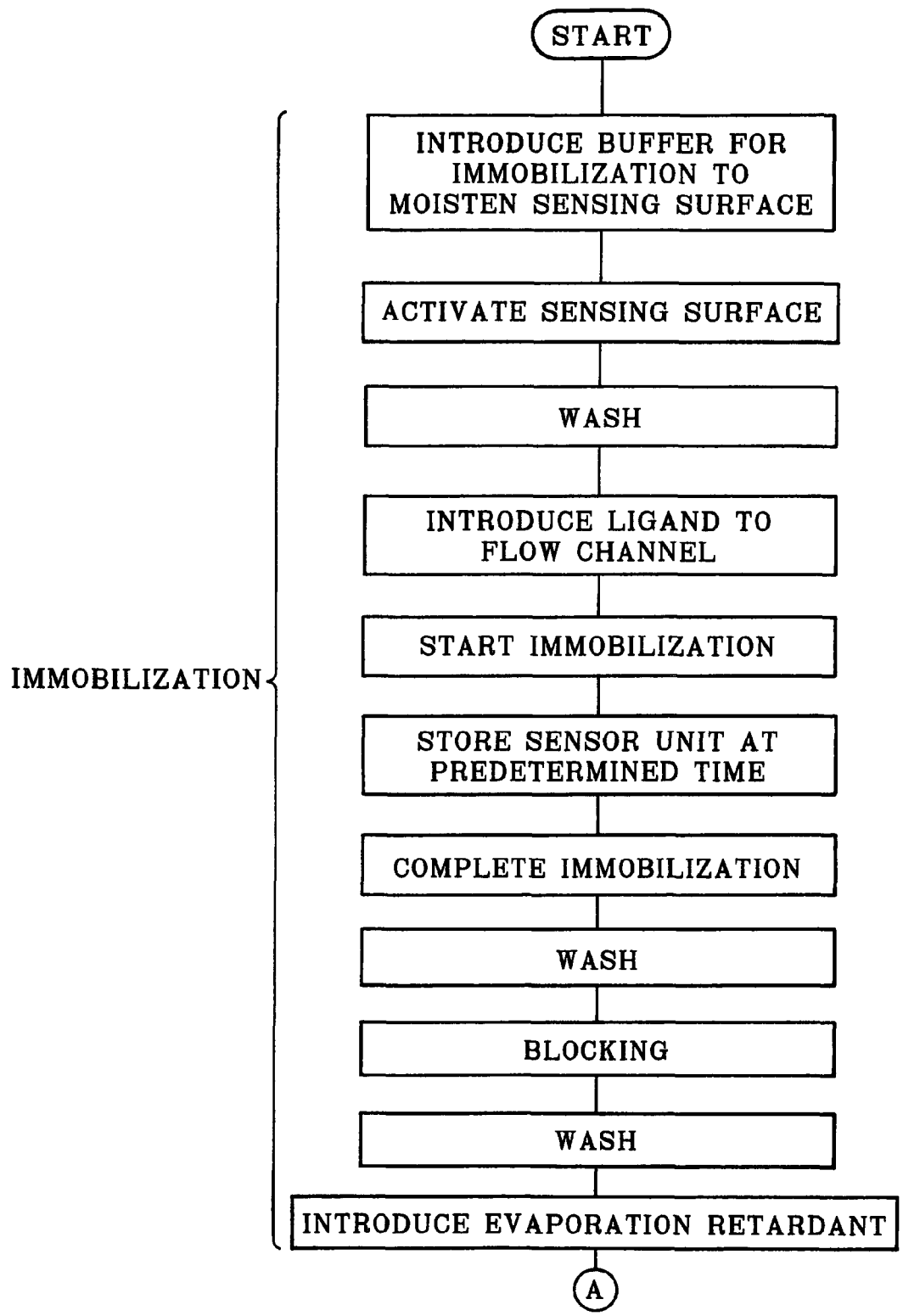
FIG. 12A is a flow chart illustrating an immobilizing process in the assay system.
Figure 12B:
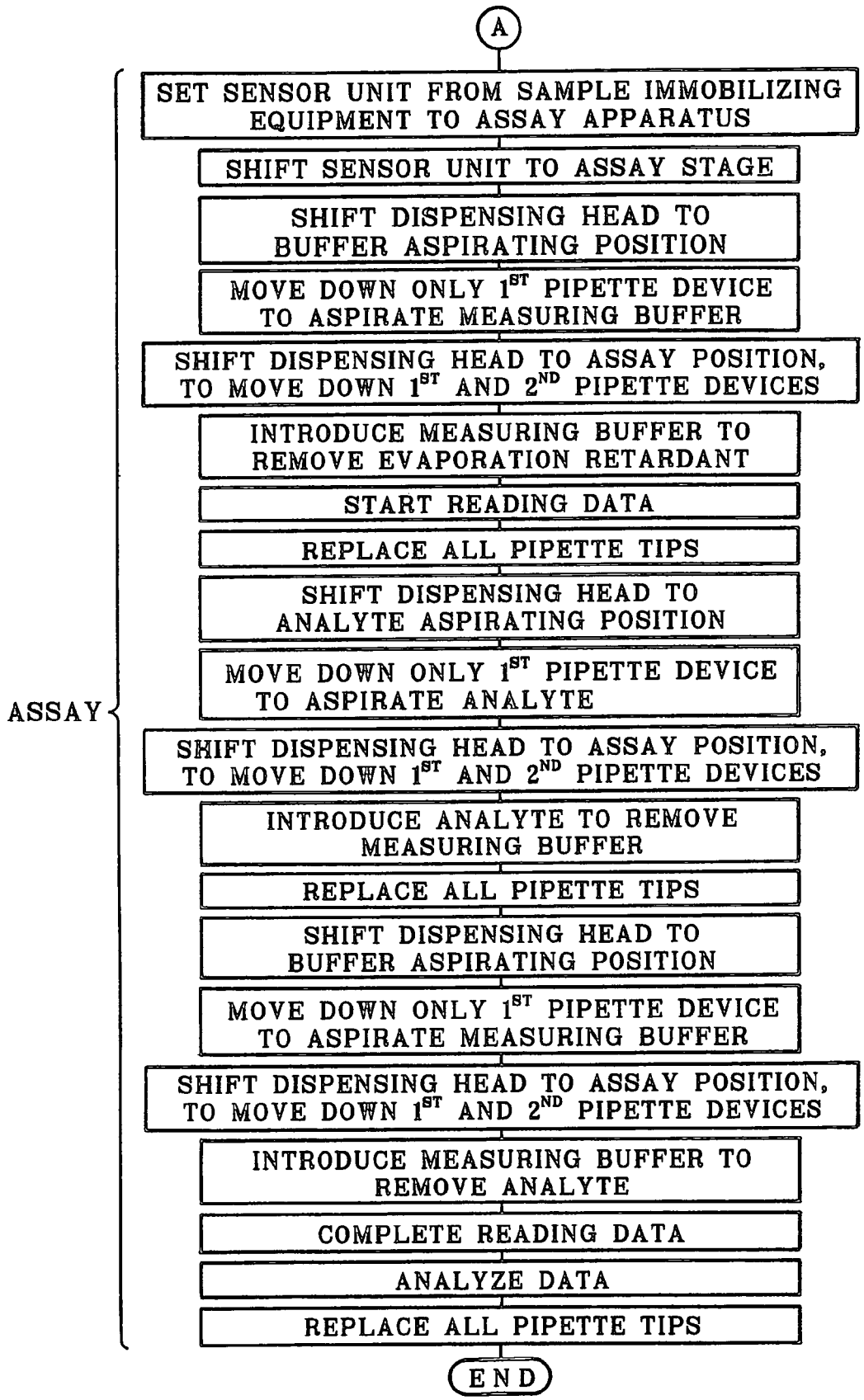
FIG. 12B is a flow chart illustrating an assay process in the assay system.

The operation is described now by referring to the flow chart of FIGS. 12A and 12B. For immobilization, the sensor unit 12 contained in the sensor holder 52 is placed in the immobilizing stage 51 of the sample immobilizing equipment 10. At first in the sample immobilizing flow, buffer for immobilization is introduced to the sensor cells 17 to wet the sensing surface 13a. Then activation fluid is introduced to activate the sensing surface 13a. After the washing, the ligand fluid 21 is introduced to the sensor cells 17 for immobilization. The sensor unit 12 is left to stand on the immobilizing stage 51 for a predetermined time. The ligand 21a in the ligand fluid becomes bound on the linker film 22 for immobilization.

When the immobilization is completed upon lapse of predetermined time, washing and blocking are effected. After the blocking step, the sensor cells 17 are washed, and provided with evaporation retardant. The sensor unit 12 is transferred to the assay apparatus 11 with the sensing surface 13a kept wet with the evaporation retardant.

A plurality of the sensor units 12 are set in the support plate 78 of the assay apparatus 11 in a state aligned in the sensor holder 52. A signal of instructing start of assay is input in the assay apparatus 11, to verify that the sensor holder 52 is set on the support plate 78. In response to the successful verification, the holder shifter 71 is actuated to set the sensor unit 12 in the standby stage.

When the sensor unit 12 before assay is set on the standby stage, the pusher shifter 83 operates to move the pusher 81 up to the standby stage, and stops the pusher 81. Then the pusher shifter 83 moves the pusher 81 further up to the clamping position. The sensor unit 12 is moved to a space between claws of the handler 82, and squeezed by the claws. The sensor unit 12 squeezed by the handler 82 is shifted by the transporting mechanism 89 to the assay stage 74.

The sensor unit 12 shifted to the assay stage 74 is finely moved in the Y direction by control of the motor 90 for the rotational angle. One of the sensor cells 17 as a target is set in the assay position. Then the dispenser shifter 73 is driven to cause the multi channel dispensing head 87 to move to the measuring buffer aspirating position.

The multi channel dispensing head 87 is moved only in the X and Y direction to come to the measuring buffer aspirating position. The first pipette head 101 is in the upper home position in the Z direction. When movement of the first pipette head 101 is completed in the X and Y directions, the stopper rods 141 become engaged with the blocking projecting rods 140 in the upward direction. The Z direction motor 112 is driven to move down the first pipette head 101. As illustrated in FIG. 9, the second pipette head 102 is kept by the stopper rods 141 from moving down.

Three first pipette devices 30 are disposed on the first pipette head 101. When the first pipette head 101 moves to the lower position, the three first pipette devices 30 access the wells 88a of the multi well plate 88 as illustrated in FIG. 13. Then the first pump 151 is actuated to aspirate the measuring buffer through the first pipette devices 30. After the aspiration to draw, the Z direction motor 112 is driven to move back the first pipette head 101 to the upper home position. The stopper 130 of the first pipette head 101 contacts the contact projection 131 of the second pipette head 102. The first and second pipette heads 101 and 102 are ready at a height with an equal height of the first and second pipette devices 30 and 35.

The dispenser shifter 73 moves the multi channel dispensing head 87 in the X and Y directions to set in the assay position. Then the Z direction motor 112 is driven to lower the first pipette head 101. As the stopper rods 141 lack in the assay position, the second pipette head 102 moves down together with the first pipette head 101 as illustrated in FIG. 10. The first and second pipette devices 30 and 35 with the pipette tips 62 are lowered with a maintained equal height. When the Z direction motor 112 is stopped, each pipette tip 62 of the first pipette device 30 is inserted in the first orifice 16a of the sensor cells 17. The second pipette device 35 is inserted in the second orifice 16b. The pumps 151 and 152 are actuated to cause the first pipette device 30 to introduce measuring buffer in the first orifice 16a. In synchronism, the second pipette device 35 aspirates evaporation retardant from the flow channel 16 and removes externally. Upon introduction of the measuring buffer in the flow channel 16, the optical assay unit 31 operates to start reading data. After the introduction, the multi channel dispensing head 87 is moved to the detipping position, to replace all the pipette tips at the first and second pipette devices 30 and 35.

After the replacement, the multi channel dispensing head 87 is driven to access the analyte fluid aspirating position. Because of the stopper rods 141, only the first pipette head 101 moves down. Only the first pipette devices 30 are inserted in the wells 88a to aspirate the analyte fluid 27. After the aspiration, the multi channel dispensing head 87 moves back to the away position. The second pipette head 102 moves down according to moving down of the first pipette head 101. Thus, the first pipette devices 30 are inserted in the first orifice 16a of the sensor cells 17. The second pipette devices 35 are inserted in the second orifice 16b. The pumps 151 and 152 are actuated to introduce analyte fluid from the first pipette device 30 to the first orifice 16a. The second pipette device 35 aspirates measuring buffer from the flow channel 16 and drains the same externally.

When analyte contacts the sensing surface 13a, interaction occurs between the analyte and ligand. After predetermined time, the first and second pipette devices 30 and 35 are both replaced. The multi channel dispensing head 87 actuates in a manner equal to the above. Measuring buffer is introduced to remove the analyte fluid. Then reading of data is terminated. The measuring data is transmitted from the photo detector 33 to the data analyzer 91, and analyzed. In this manner, each one of the plurality of the sensor cells 17 is subjected to the assay. The sensor unit 12 after the assay is returned to the clamping position, and then returned to the sensor holder 52.

The sensor unit 12 after the assay is returned to and contained in the sensor holder 52. After this, the holder shifter 71 is actuated to shift the support plate 78 by one step equal to the pitch, to shift a second sensor unit 12 to the standby stage. The steps of the above process are repeated to feed the sensor units 12 to the assay stage one after another.

Note that the stopper rods 141 may be disposed on the multi channel dispensing head 87 instead of disposition in the above described aspirating positions determined in the assay apparatus. In combination with this, the stopper rods 141 can be disposed on the support frame 111 as a fixed component besides the first and second pipette heads 101 and 102. The stopper rods 141 are kept movable between first and second positions, and when in the first position, is engaged with the blocking projecting rods 140 in the upward direction, and when in the second direction, comes away from the blocking projecting rods 140 for disengagement. An actuator such as a solenoid or electric cylinder can move and set the stopper rods 141 in a selected one of the first and second positions.

In the above embodiment, the first and second pipette heads 101 and 102 are moved vertically or in the Z direction. However, the Z direction according to the invention may be any direction that is crosswise to the X and Y directions. Also, any structure operating mechanically may be utilized by way of the first guide mechanism 103, the second guide mechanism 105, the driving mechanism 104 and the moving unit 100 of the X and Y directions in a manner different from the above embodiment.

In the above embodiment, the assay apparatus 11 having the assay stage has a first casing distinct from a second casing of the sample immobilizing equipment 10 having the immobilizing stage. However, a single casing may be used, and may include the immobilizing stage and assay stage to use the multi channel fluid dispenser 18 in a common manner. Furthermore, the multi channel fluid dispenser 18 of the invention may be a type for any purpose and with a dispensing head having a pair of pipette nozzles for aspiration and dispensation of fluid. The multi channel fluid dispenser 18 of the invention may be used in the sample immobilizing equipment 10 in a specialized use.

In the above embodiment, the three first pipette devices 30 and the three second pipette devices 35 are disposed in the first and second pipette heads 101 and 102. The three flow channels 16 can be accessed by three dual pipette assemblies 26 for assay simultaneously. However, the number of the dual pipette assemblies 26 may be one or two, or four or more.

In addition to the SPR sensor, an assay sensor unit in combination with the fluid dispenser of the invention can be other sensor in utilizing attenuated total reflection. One example of sensor unit according to utilizing the attenuated total reflection is a leaky mode sensor. The leaky mode sensor includes a dielectric medium, a cladding layer overlaid on the dielectric medium, and an optical waveguide layer overlaid on the cladding layer, those layers constituting a thin film. A first surface of the thin film is a sensing surface on the optical waveguide layer. A second surface of the thin film is a metal/dielectric interface on the cladding layer. When light becomes incident on the metal/dielectric interface to satisfy the condition of the total reflection, part of the light passes through the cladding layer, and enters the optical waveguide layer. A guided mode to propagate light is excited responsively in the optical waveguide layer, to attenuate the reflected light on the metal/dielectric interface. An angle of the incidence at which the guided mode is excited is changeable according to the refractive index of the medium positioned on the sensing surface. This is similar to the characteristic of the resonance angle of the SPR sensor. The attenuation of the reflected light is detected, so that it possible to measure the interaction on the sensing surface.

Although the present invention has been fully described by way of the preferred embodiments thereof with reference to the accompanying drawings, various changes and modifications will be apparent to those having skill in this field. Therefore, unless otherwise these changes and modifications depart from the scope of the present invention, they should be construed as included therein.

What is claimed is:

1. An assay apparatus comprising:
a multi well plate, comprising a plurality of wells;
a sample contained in said plurality of wells;
a sensor unit comprising a flow channel and a sensing surface disposed in said flow channel, said sensing surface configured to assay reaction of said sample flowing through said flow channel;
stopper rods;
an assay unit configured to position said sensor unit for assay; and
a fluid dispenser comprising:
a dispensing head, comprising a first head and a second head, movable between an aspirating position and an assay position,
wherein the dispensing head is configured to aspirate said sample by accessing one of said plurality of wells in said multi well plate in a downward accessing direction, when in said aspirating position; and
wherein the fluid dispenser head is configured to introduce said sample by accessing in a downward accessing direction into said flow channel in said sensor unit, when in said assay position,
wherein said first head supports a first pipette device,
wherein said first pipette device comprises a first pipette tip, and is configured to be set in said well and aspirate said sample, and set in a first orifice of said flow channel to dispense said sample;
wherein said second head supports a second pipette device,
wherein said second pipette device comprises a second pipette tip, and is configured to be set in a second orifice of said flow channel and aspirate fluid in synchronism with dispensation said sample by said first pipette device; a driving mechanism configured to shift up or down said first head to move between a first position and a second position,
wherein said first position positions said first pipette tip in said well or said first orifice, and said second position positions said first head higher than said first position and said first pipette tip away from said well or said first orifice;
a guide mechanism configured to support said second head movably in a vertical shifting direction of said first head and relatively thereto;
a stopper portion of said first head configured to engage said second head when said second pipette tip is positioned at substantially the same height as said pipette tip of said first pipette device, preventing said second head from moving further downwards;
a biasing mechanism for biasing said second head toward said stopper portion, wherein said stopper rods are configured to engage said second head when said dispensing head is in said aspirating position, preventing said second head from moving down together with said first head against a bias of said biasing mechanism.

2. The assay apparatus according to claim 1, wherein said second head comprises:

a plurality of lateral sides; and projecting rods protruding from each of said plurality of lateral sides of said second head and engaging with said stopper rods.

3. The assay apparatus according to claim 1, wherein said guide mechanism comprises:

a slide rail portion formed on said first head; and a slidable portion formed with said second head engaging with said slide rail portion in a slidable manner.

4. The assay apparatus according to claim 1, wherein said first head comprises a plurality of said first pipette device, and said second head comprises a plurality of said second pipette devices.

5. The assay apparatus according to claim 1, further comprising a position sensor configured to detect said first head in said second position.

6. The assay apparatus according to claim 1, further comprising a controller.

7. The assay apparatus according to claim 2, further comprising a controller.

8. The assay apparatus according to claim 3, further comprising a controller.

9. The assay apparatus according to claim 4, further comprising a controller.

10. The assay apparatus according to claim 5, further comprising a controller.

* * * * *